(12) United States Patent
Igami

(10) Patent No.: US 11,786,136 B2
(45) Date of Patent: Oct. 17, 2023

(54) INFORMATION PROCESSING APPARATUS, AND INFORMATION PROCESSING METHOD

(71) Applicant: SONY CORPORATION, Tokyo (JP)

(72) Inventor: Toru Igami, Tokyo (JP)

(73) Assignee: SONY CORPORATION, Tokyo (JP)

( * ) Notice: Subject to any disclaimer, the term of this patent is extended or adjusted under 35 U.S.C. 154(b) by 649 days.

(21) Appl. No.: 16/622,454

(22) PCT Filed: Apr. 4, 2018

(86) PCT No.: PCT/JP2018/014438
§ 371 (c)(1),
(2) Date: Dec. 13, 2019

(87) PCT Pub. No.: WO2019/003549
PCT Pub. Date: Jan. 3, 2019

(65) Prior Publication Data
US 2020/0155018 A1    May 21, 2020

(30) Foreign Application Priority Data
Jun. 28, 2017    (JP) .................. 2017-125779

(51) Int. Cl.
*A61B 5/024*    (2006.01)
*A61B 5/00*    (2006.01)

(52) U.S. Cl.
CPC ...... *A61B 5/02405* (2013.01); *A61B 5/02438* (2013.01); *A61B 5/02444* (2013.01); *A61B 5/7221* (2013.01)

(58) Field of Classification Search
None
See application file for complete search history.

(56) References Cited

U.S. PATENT DOCUMENTS

| | | | |
|---|---|---|---|
| 5,759,156 | A | 6/1998 | Hayakawa |
| 5,865,756 | A | 2/1999 | Peel, III |
| 2005/0240112 | A1 | 10/2005 | Fang |
| 2011/0245688 | A1 | 10/2011 | Arora et al. |

(Continued)

FOREIGN PATENT DOCUMENTS

| | | |
|---|---|---|
| CN | 102247141 A | 11/2011 |
| CN | 106037702 A | 10/2016 |

(Continued)

OTHER PUBLICATIONS

Office Action of JP for Patent Application No. 2019-526158, dated Nov. 24, 2021, 04 pages of English Translation and 05 pages of Office Action.

(Continued)

*Primary Examiner* — Jay B Shah
(74) *Attorney, Agent, or Firm* — CHIP LAW GROUP

(57) ABSTRACT

There is provided an information processing apparatus including a reliability degree calculation section that calculates a reliability degree of pulsation variability data or a body index; and a control unit that controls various kinds of processing on the basis of the calculated reliability degree. The pulsation variability data is acquired from sensing data acquired by a pulse wave sensor worn by a user. The body index is calculated from the pulsation variability data and indicates a physical state of the user.

20 Claims, 24 Drawing Sheets

(56) References Cited

U.S. PATENT DOCUMENTS

| | | | | |
|---|---|---|---|---|
| 2012/0296571 | A1* | 11/2012 | Shinoda | G16H 20/30 |
| | | | | 702/19 |
| 2013/0217979 | A1 | 8/2013 | Blackadar | |
| 2016/0302680 | A1 | 10/2016 | Narusawa et al. | |
| 2017/0065228 | A1* | 3/2017 | Hirano | A61B 5/02416 |

FOREIGN PATENT DOCUMENTS

| | | |
|---|---|---|
| EP | 2524647 A1 | 11/2012 |
| EP | 3081157 A1 | 10/2016 |
| EP | 3120763 A1 | 1/2017 |
| JP | H05184547 A | 7/1993 |
| JP | 07-284482 A | 10/1995 |
| JP | H07-284482 A | 10/1995 |
| JP | 07-313477 A | 12/1995 |
| JP | H07-313477 A | 12/1995 |
| JP | 2009-261419 A | 11/2009 |
| JP | 2010-162282 A | 7/2010 |
| JP | 2011-212441 A | 10/2011 |
| JP | 2015-080624 A | 4/2015 |
| JP | 2015-80624 A | 4/2015 |
| JP | 2016-146994 A | 8/2016 |
| JP | 2016-202348 A | 12/2016 |
| WO | 2014101466 A1 | 7/2014 |
| WO | 2015/141216 A1 | 9/2015 |
| WO | 2015141216 A1 | 9/2015 |
| WO | 2016194490 A1 | 12/2016 |

OTHER PUBLICATIONS

International Search Report and Written Opinion of PCT Application No. PCT/JP2018/014438, dated Jun. 19, 2018, 11 pages of ISRWO.

Office Action for CN Patent Application No. 201880041816.5, dated Apr. 27, 2022, 113 pages.

* cited by examiner

[FIG. 1]
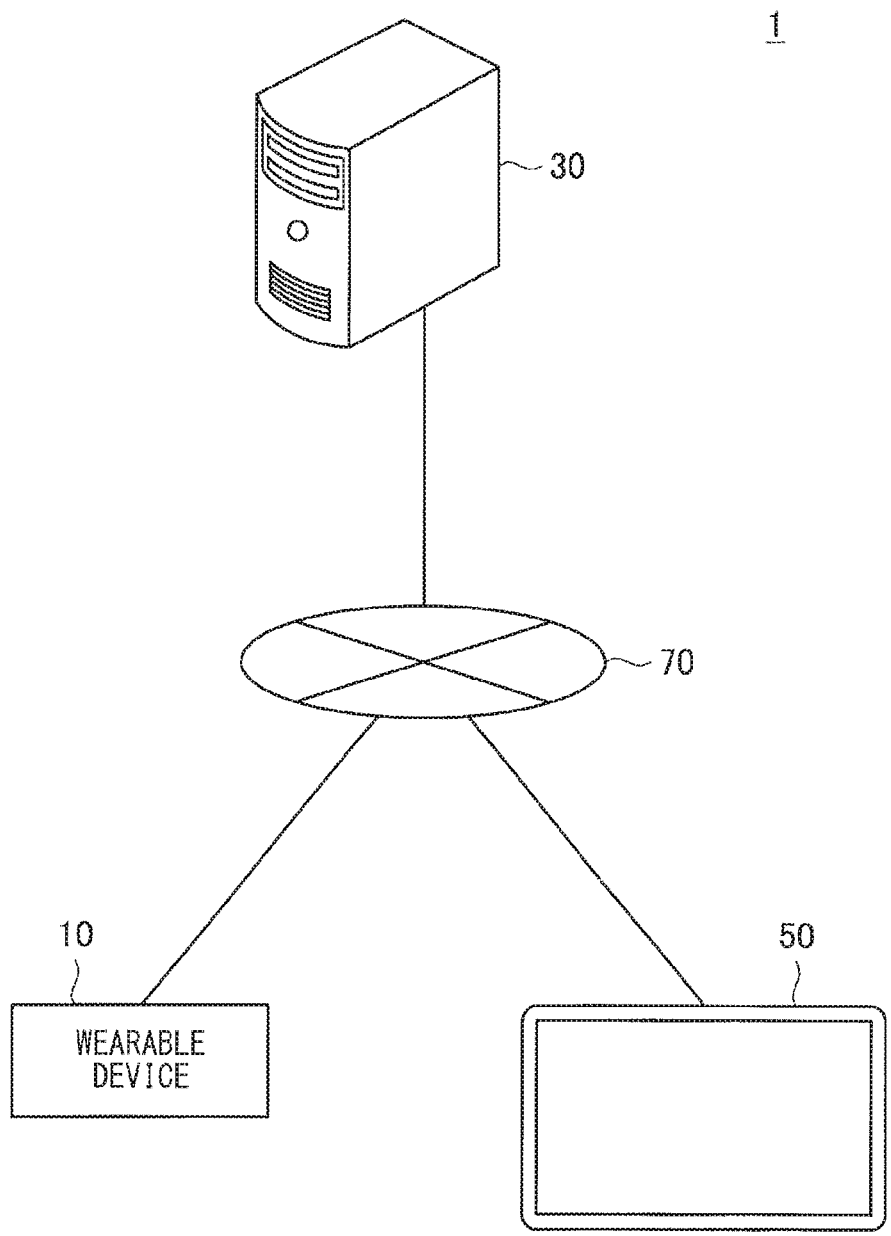

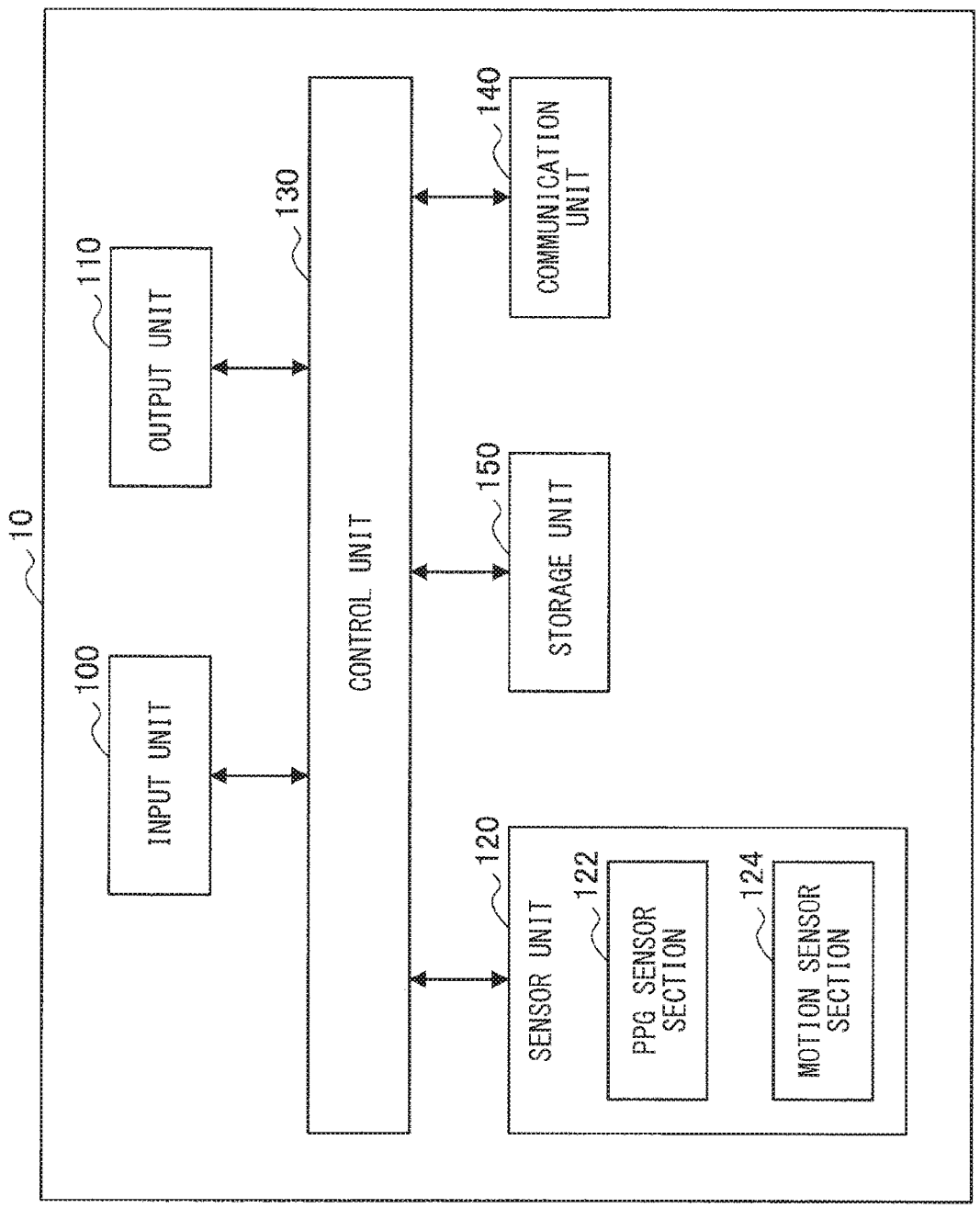
[FIG. 2]

[FIG. 3]
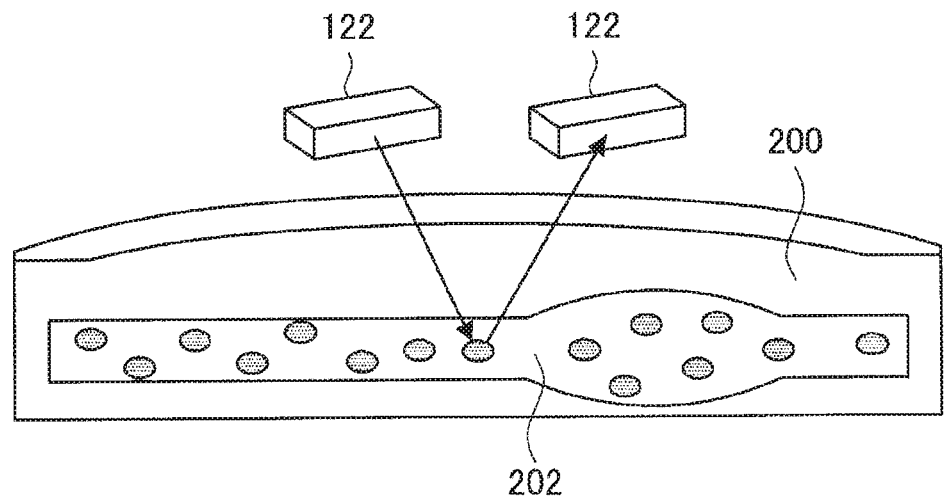

[FIG. 4]
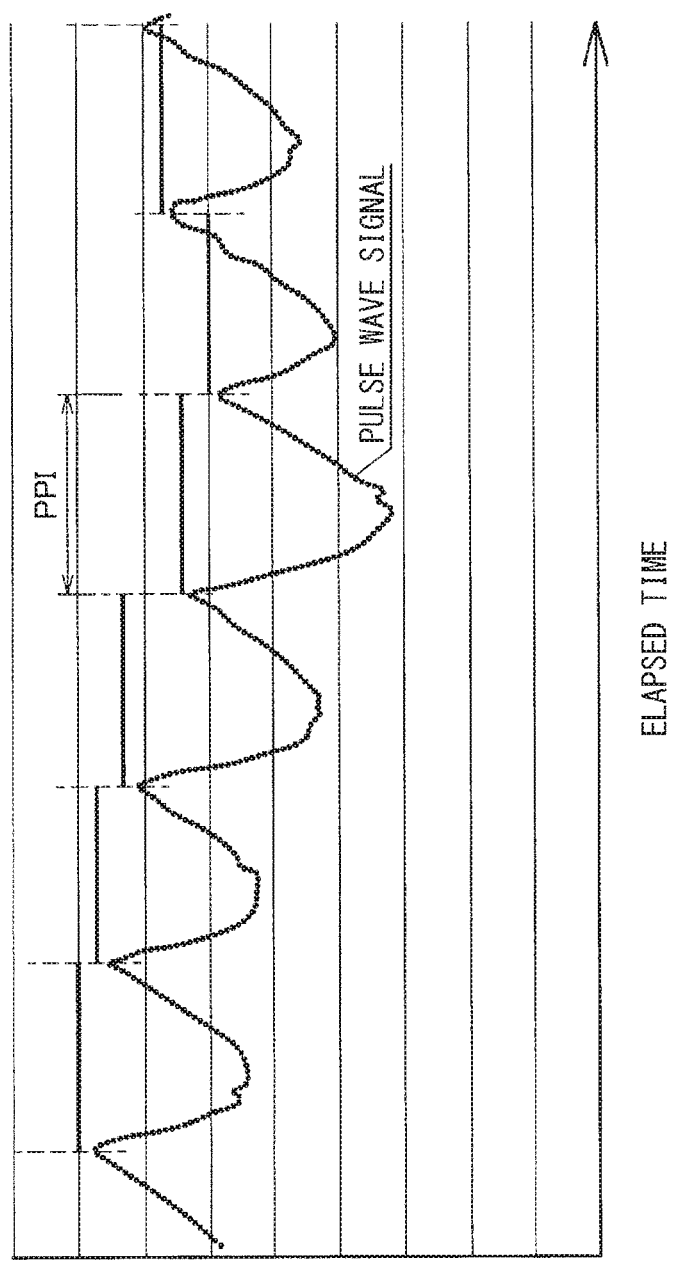

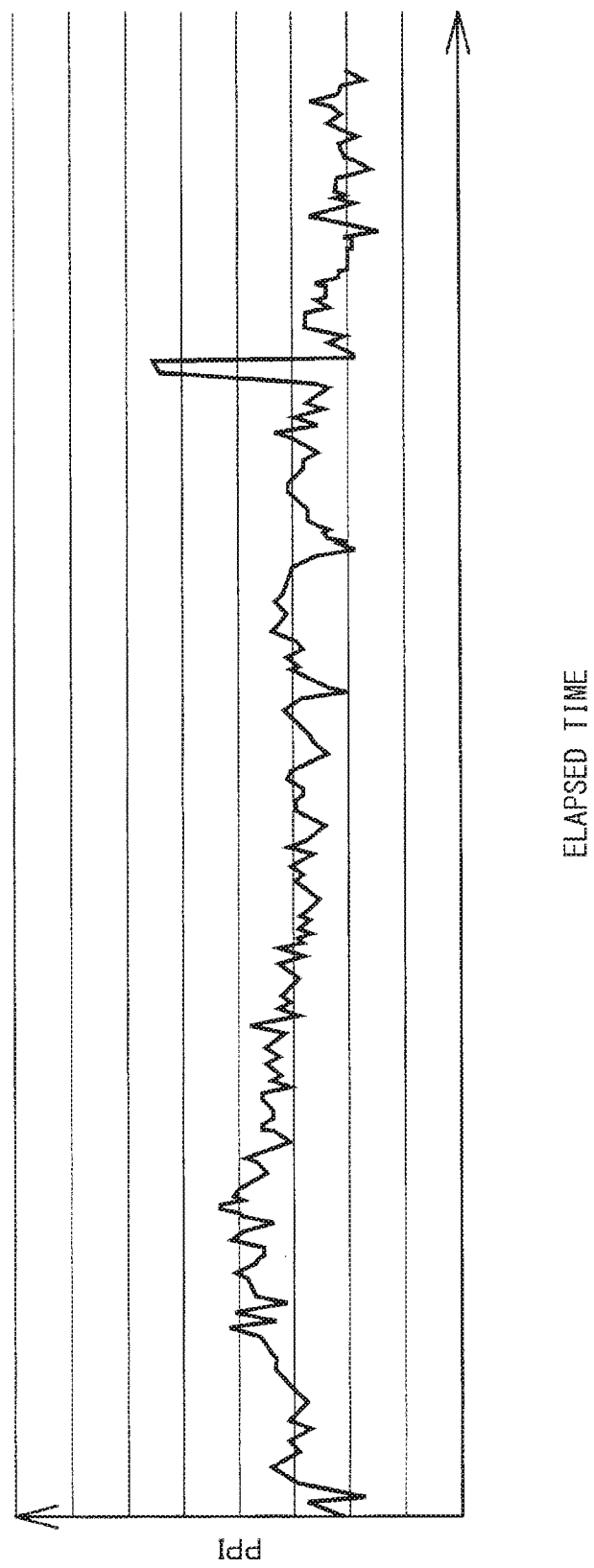
[FIG. 5]

[FIG. 6]
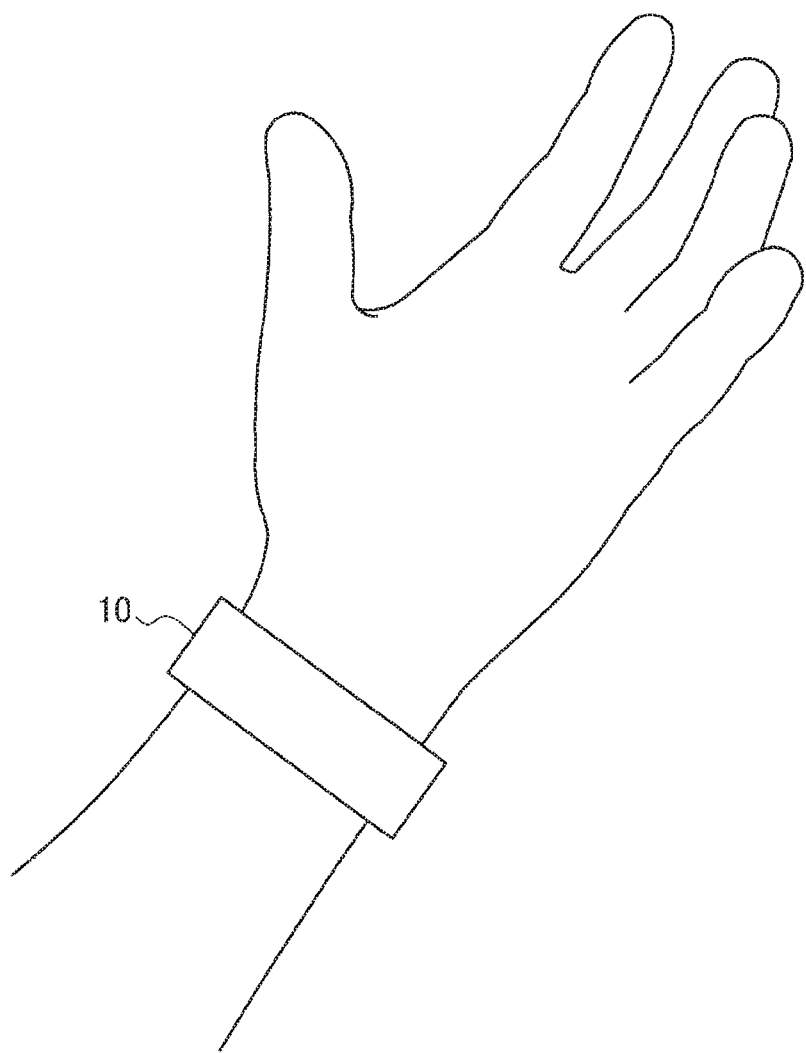

[FIG. 7]
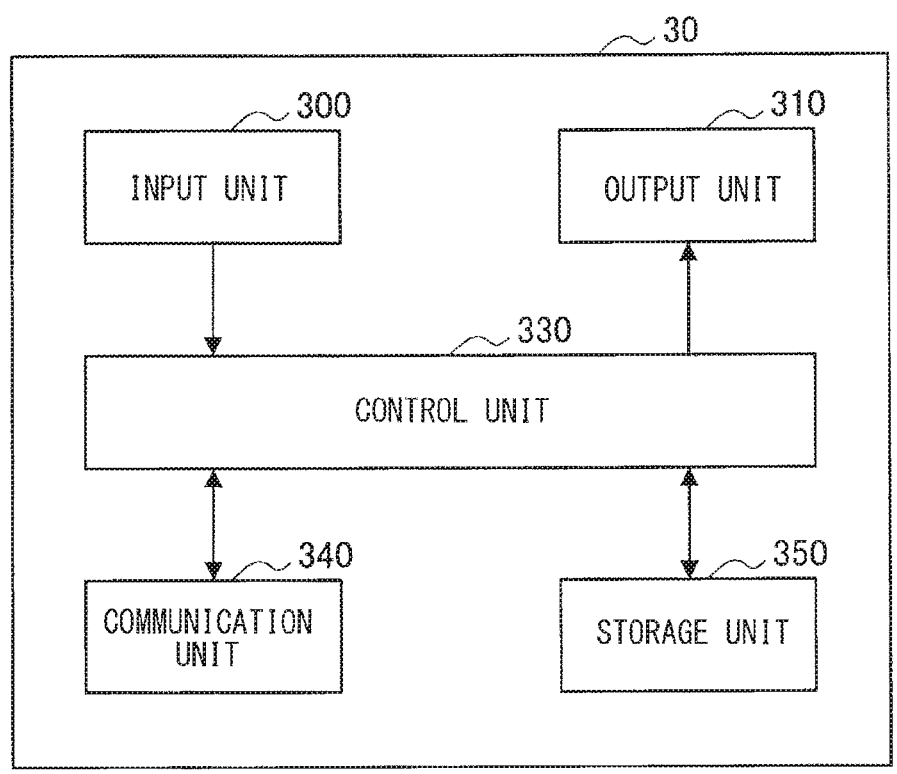

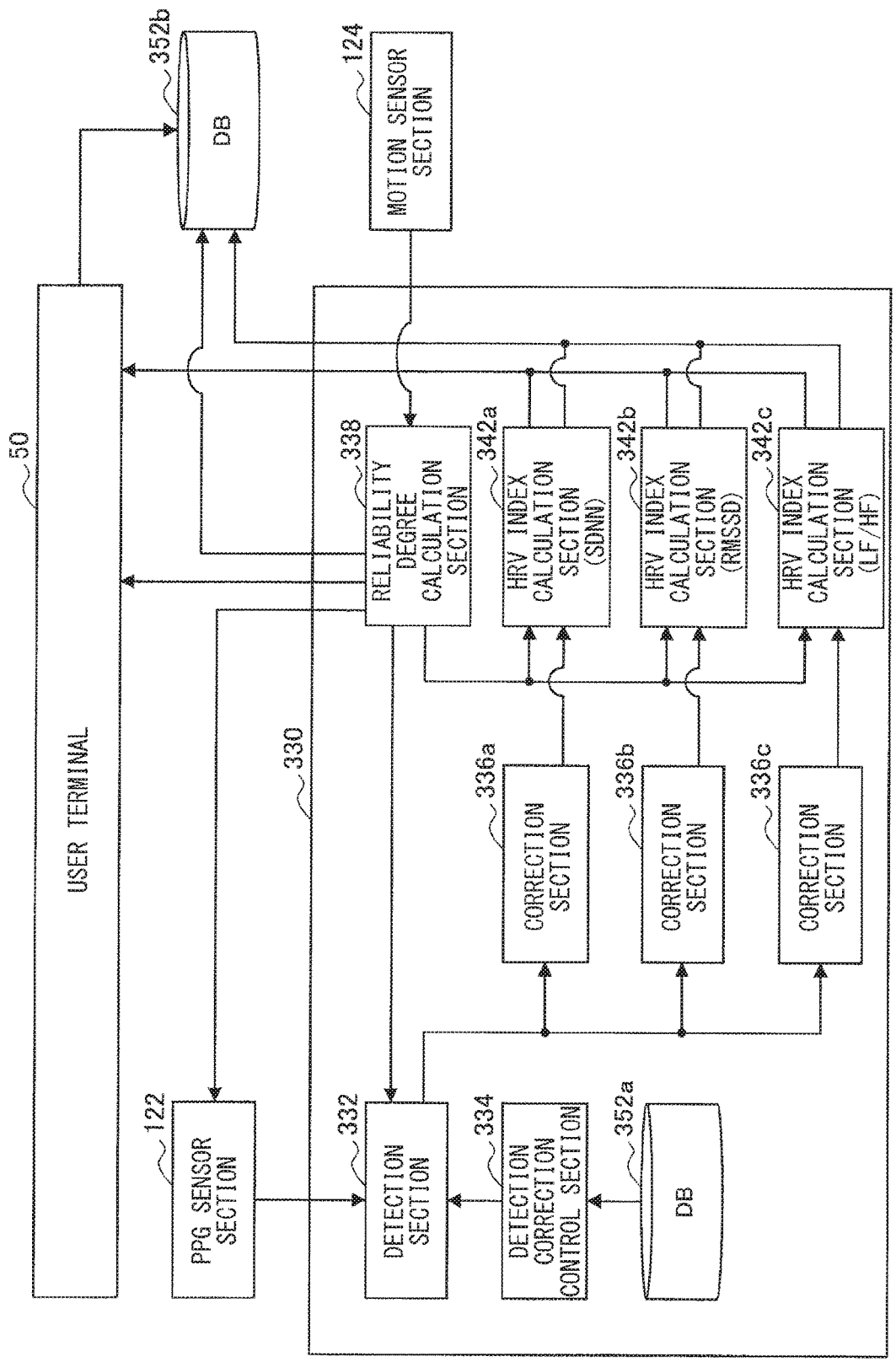

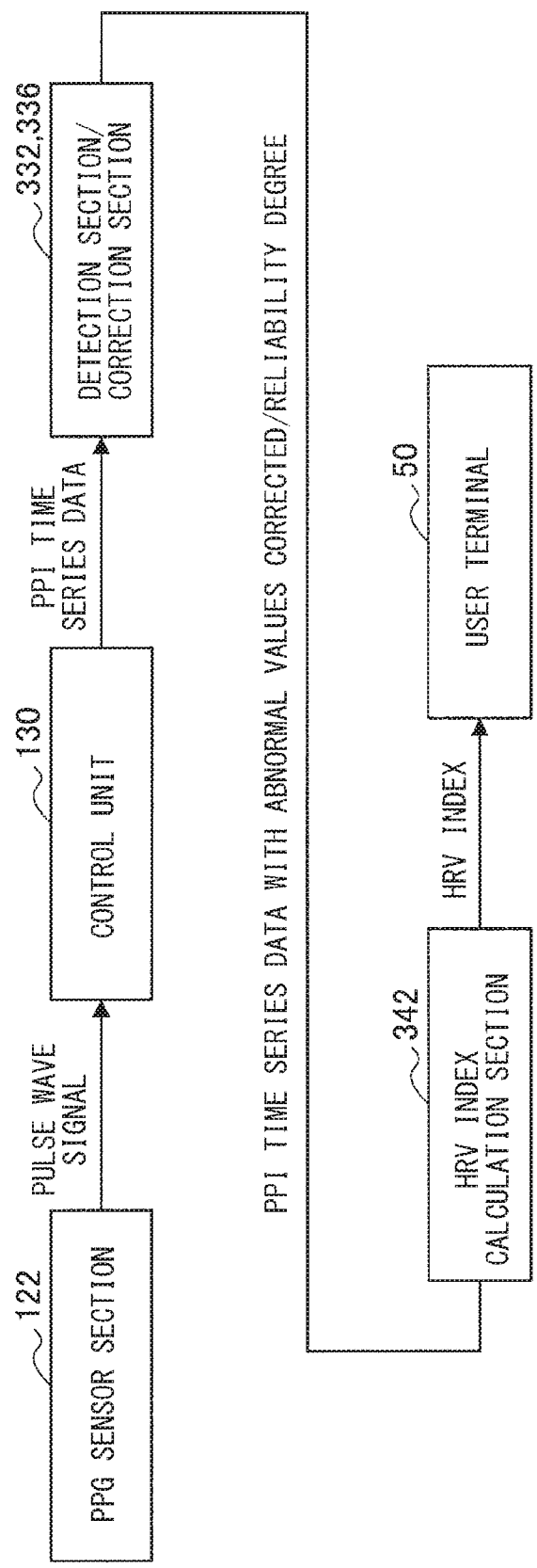
[FIG. 9]

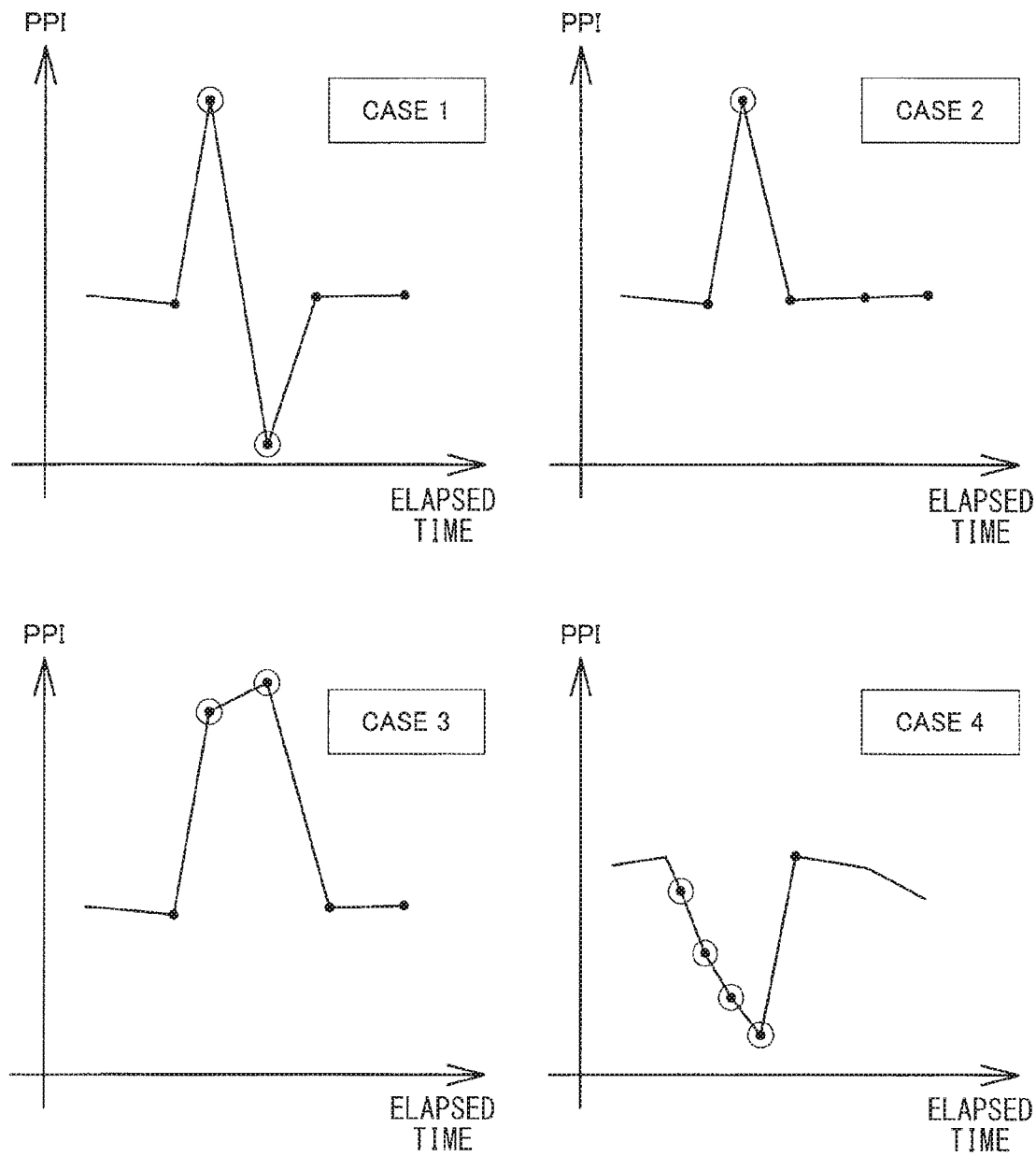
[FIG. 10]

[FIG. 11]
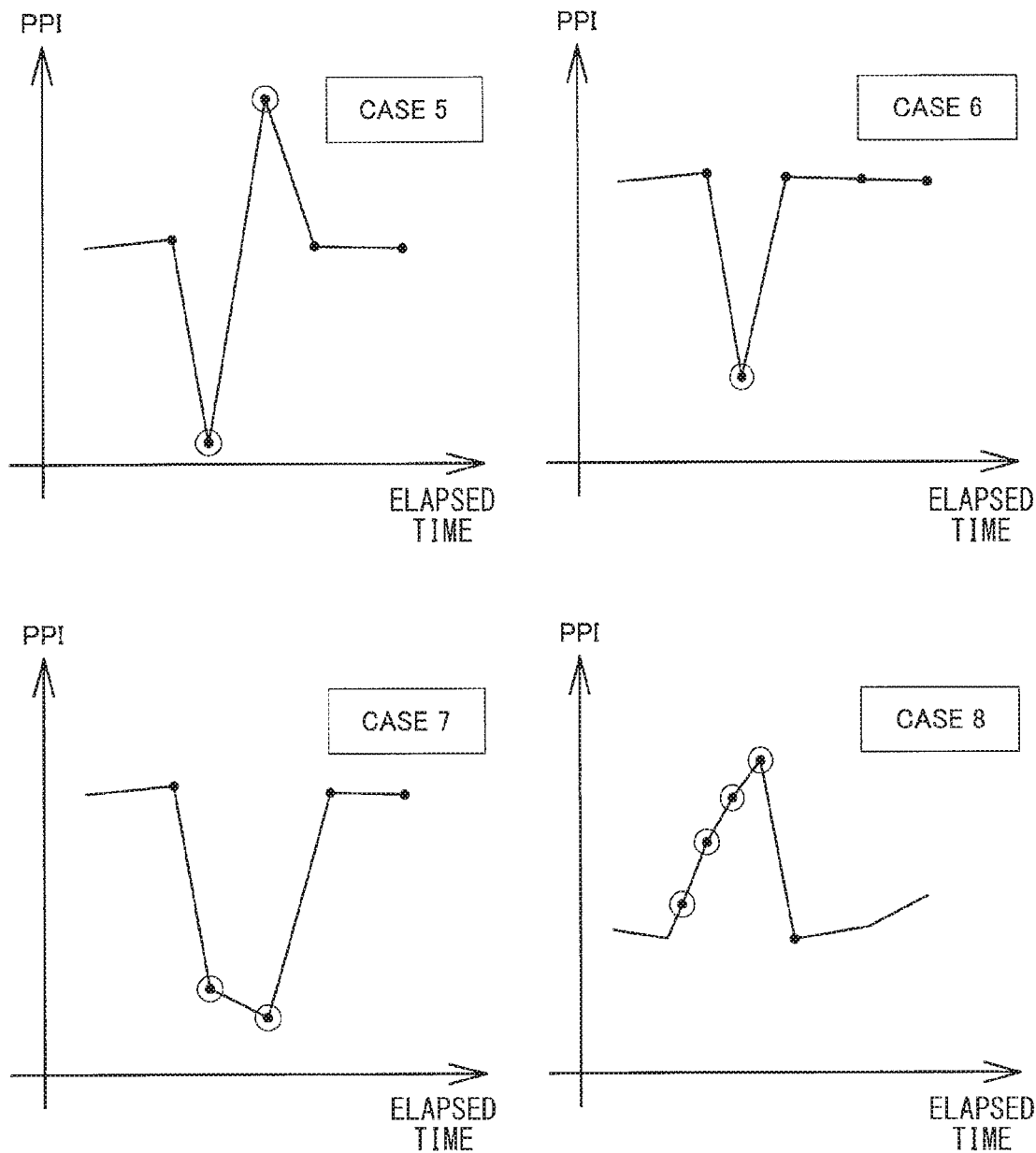

[ FIG. 12 ]
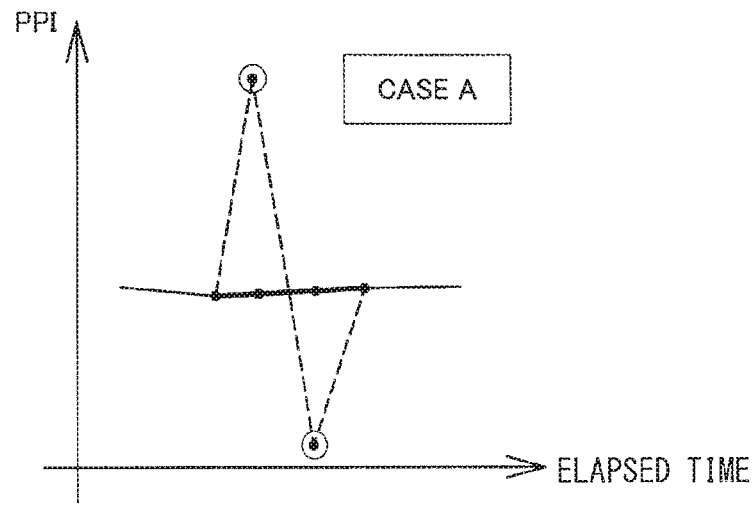
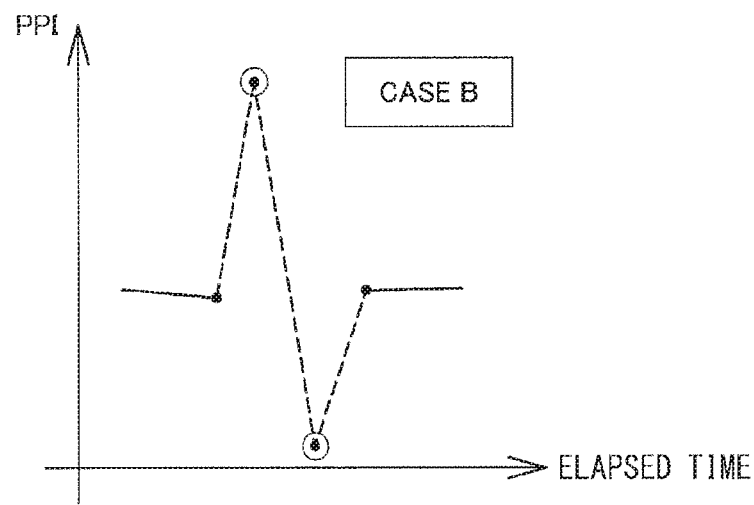
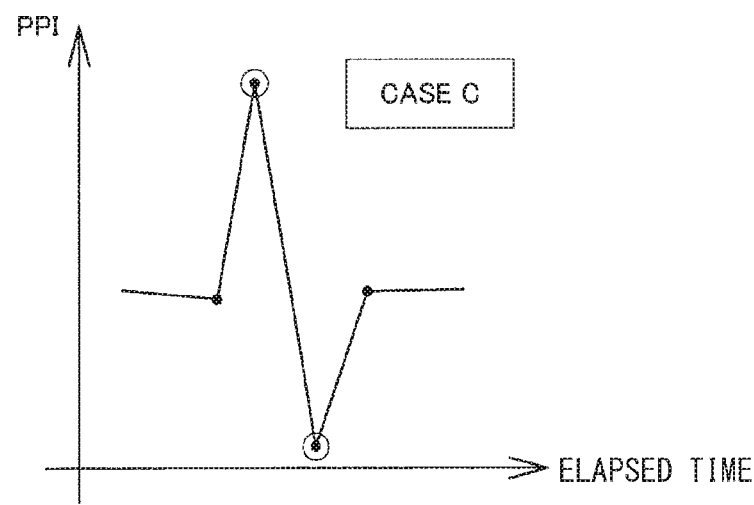

[FIG. 13]
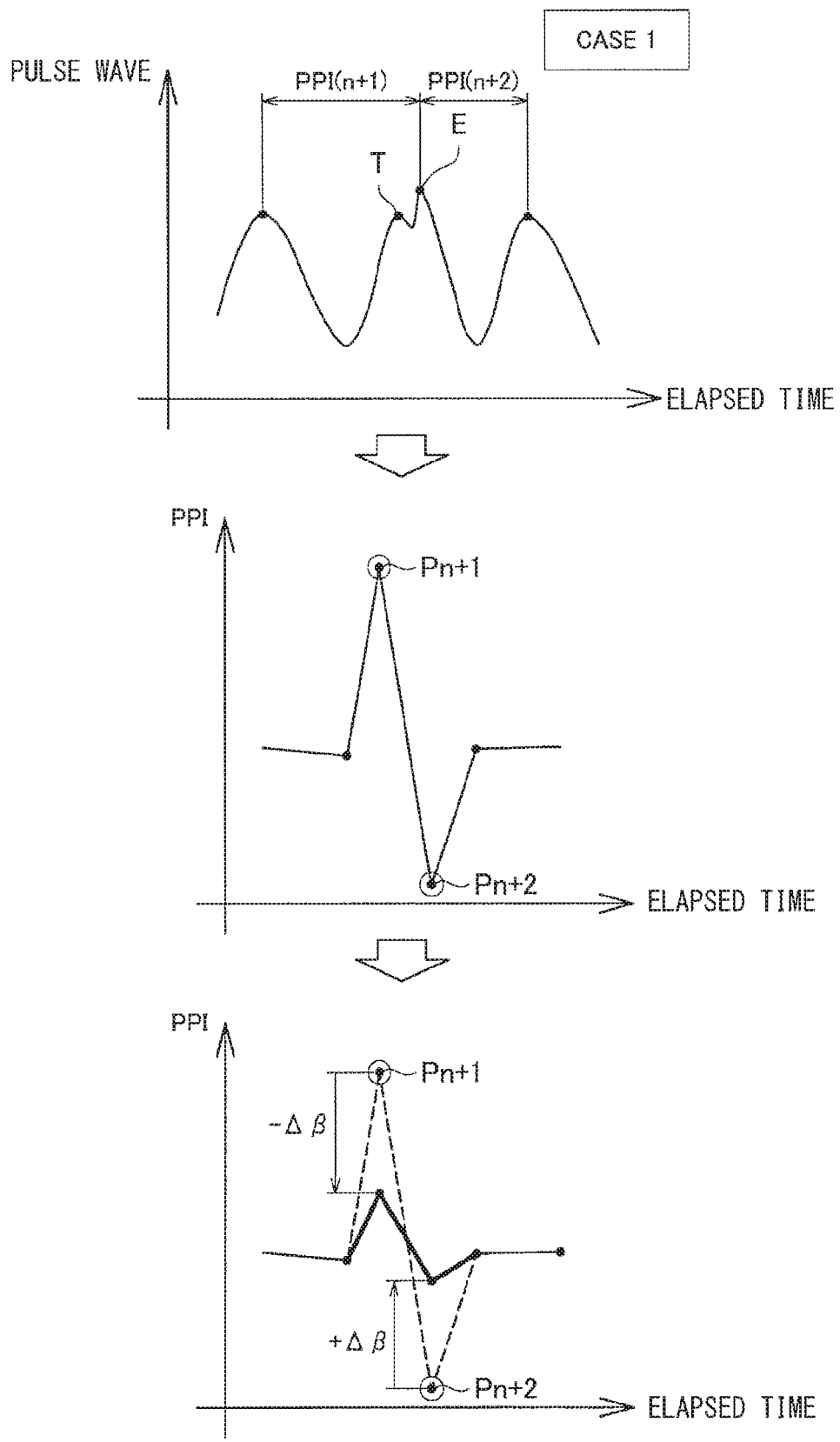

[FIG. 14]
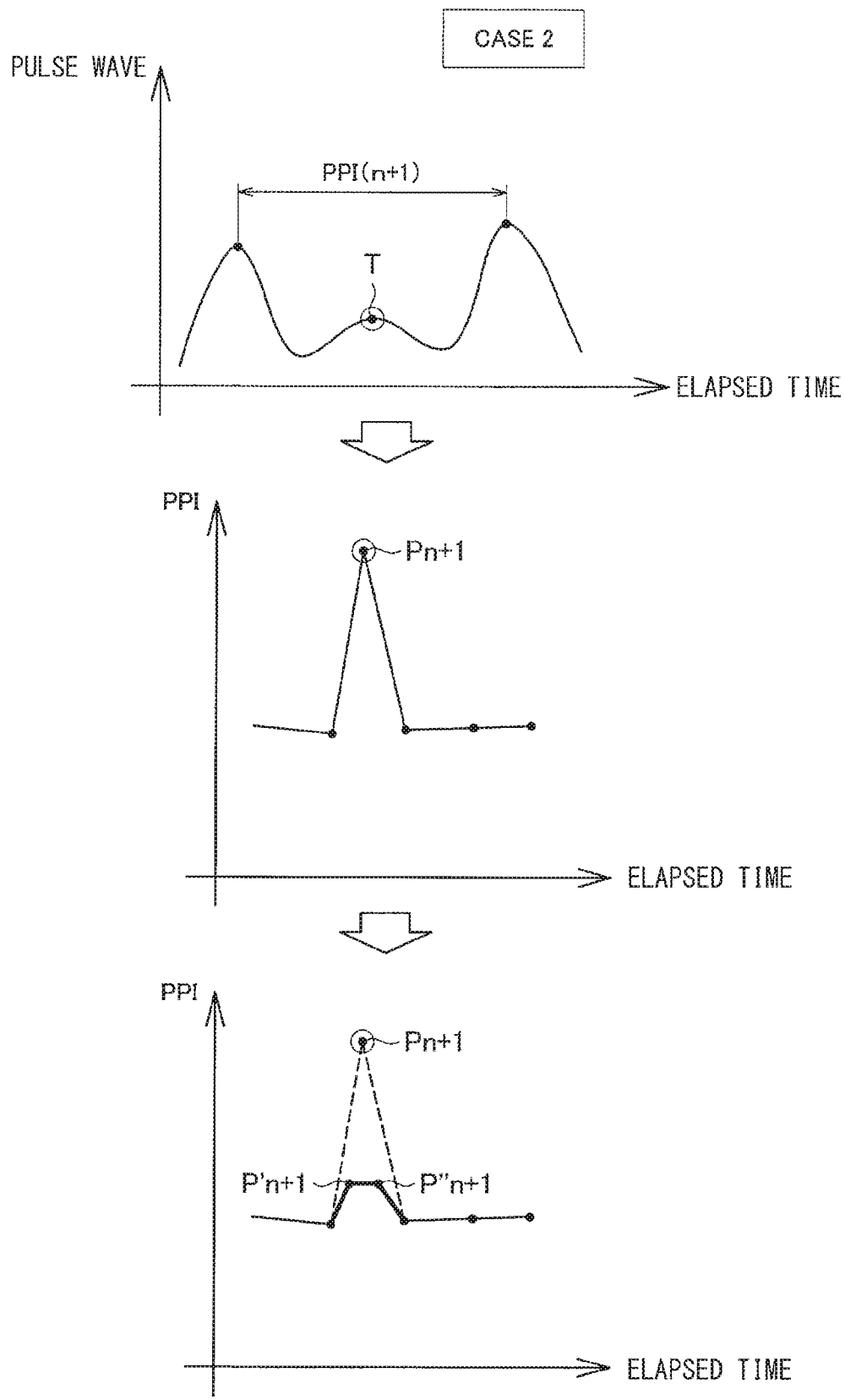

[FIG. 15]
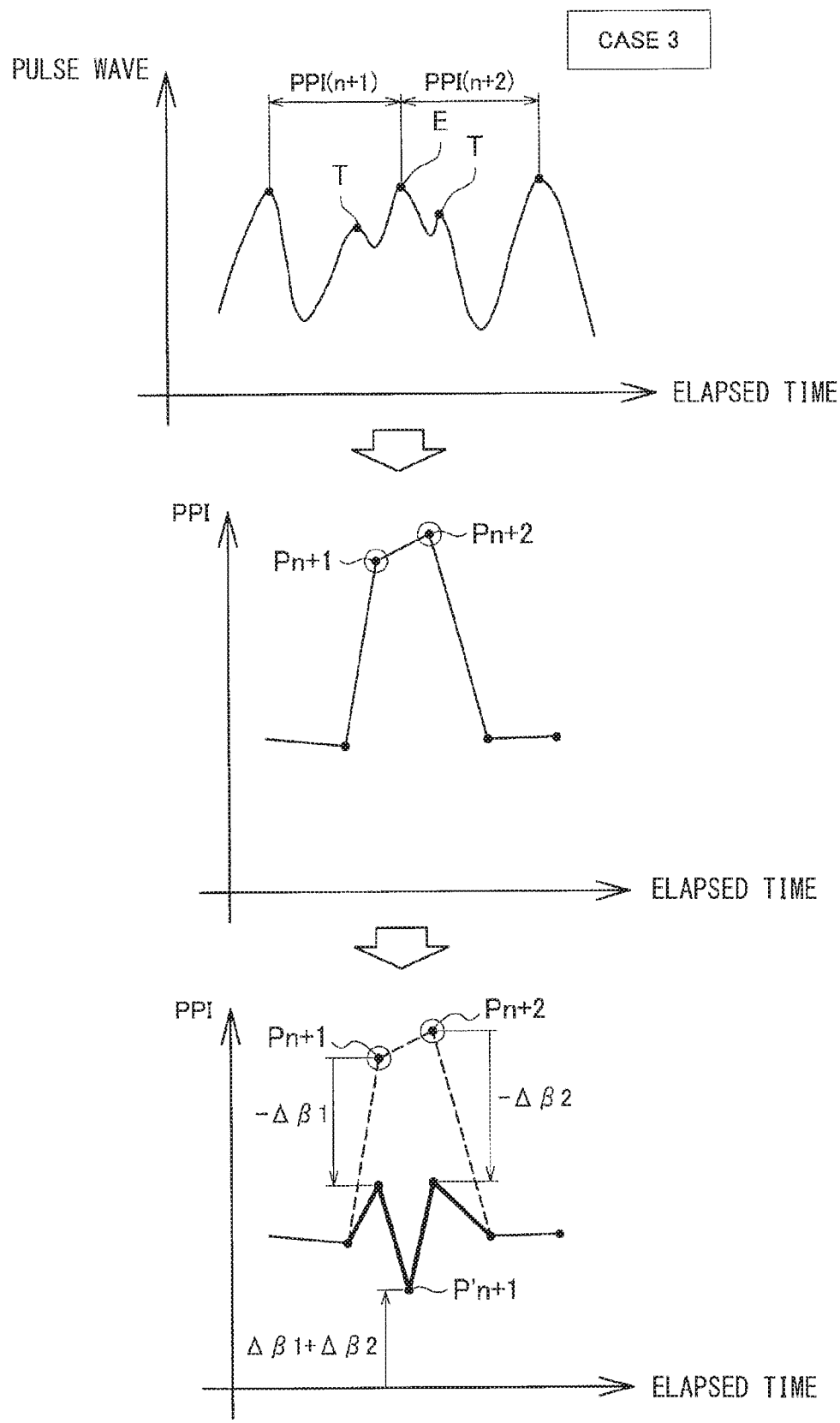

[ FIG. 16 ]
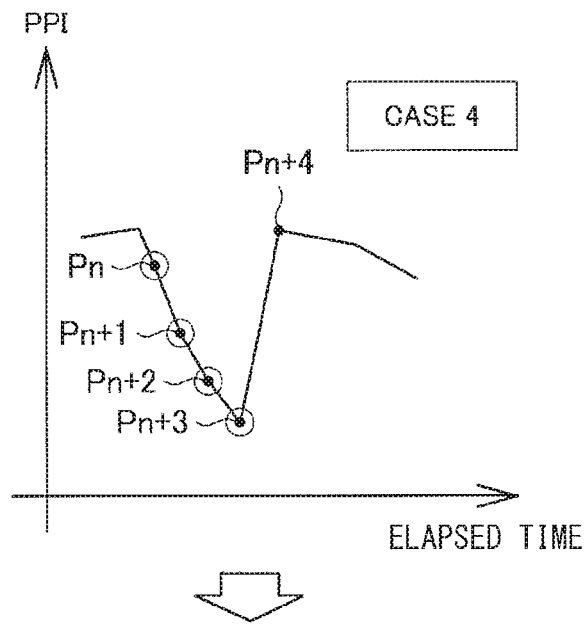
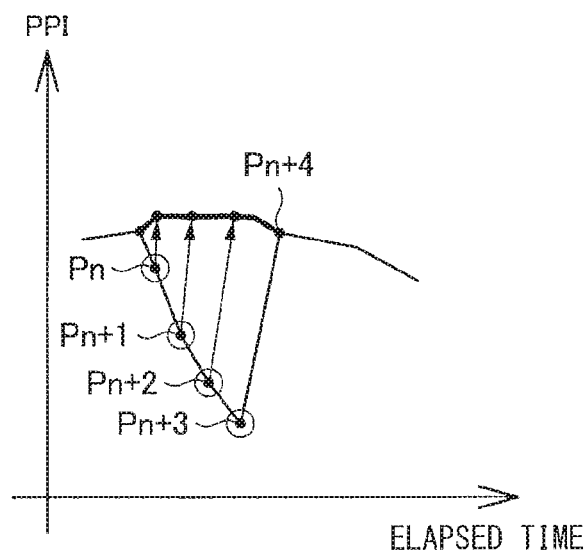

[ FIG. 17 ]
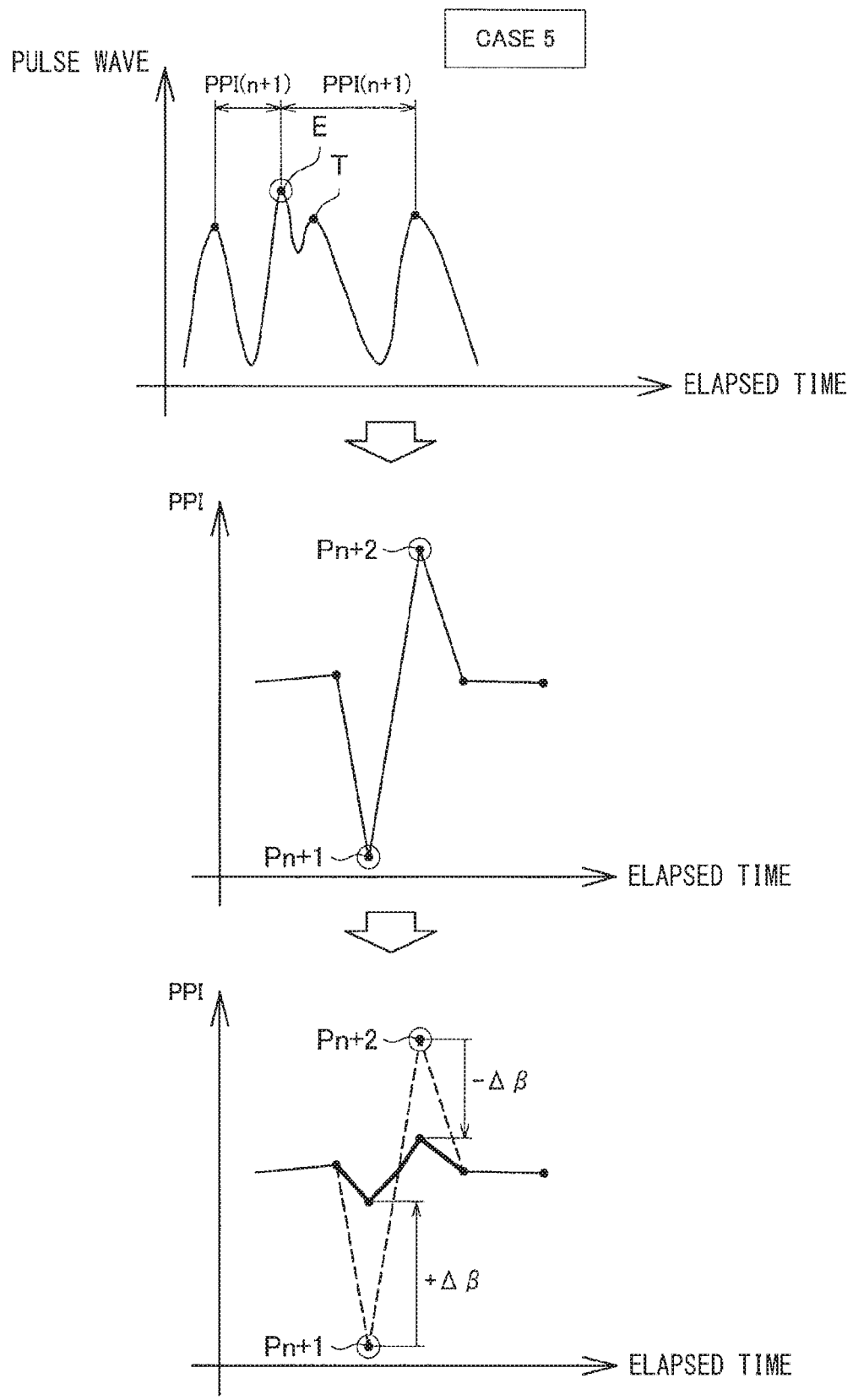

[ FIG. 18 ]
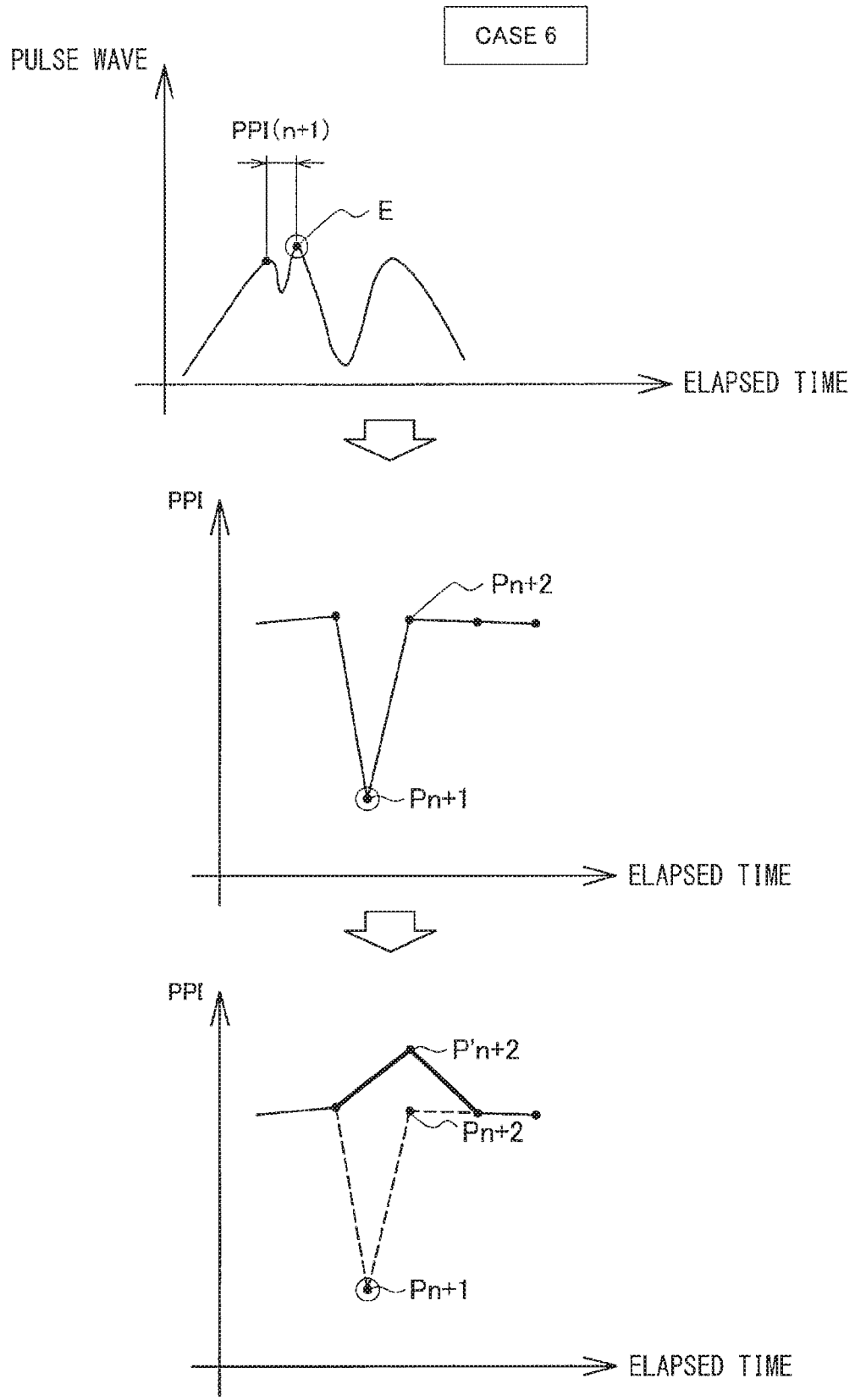

[FIG. 19]
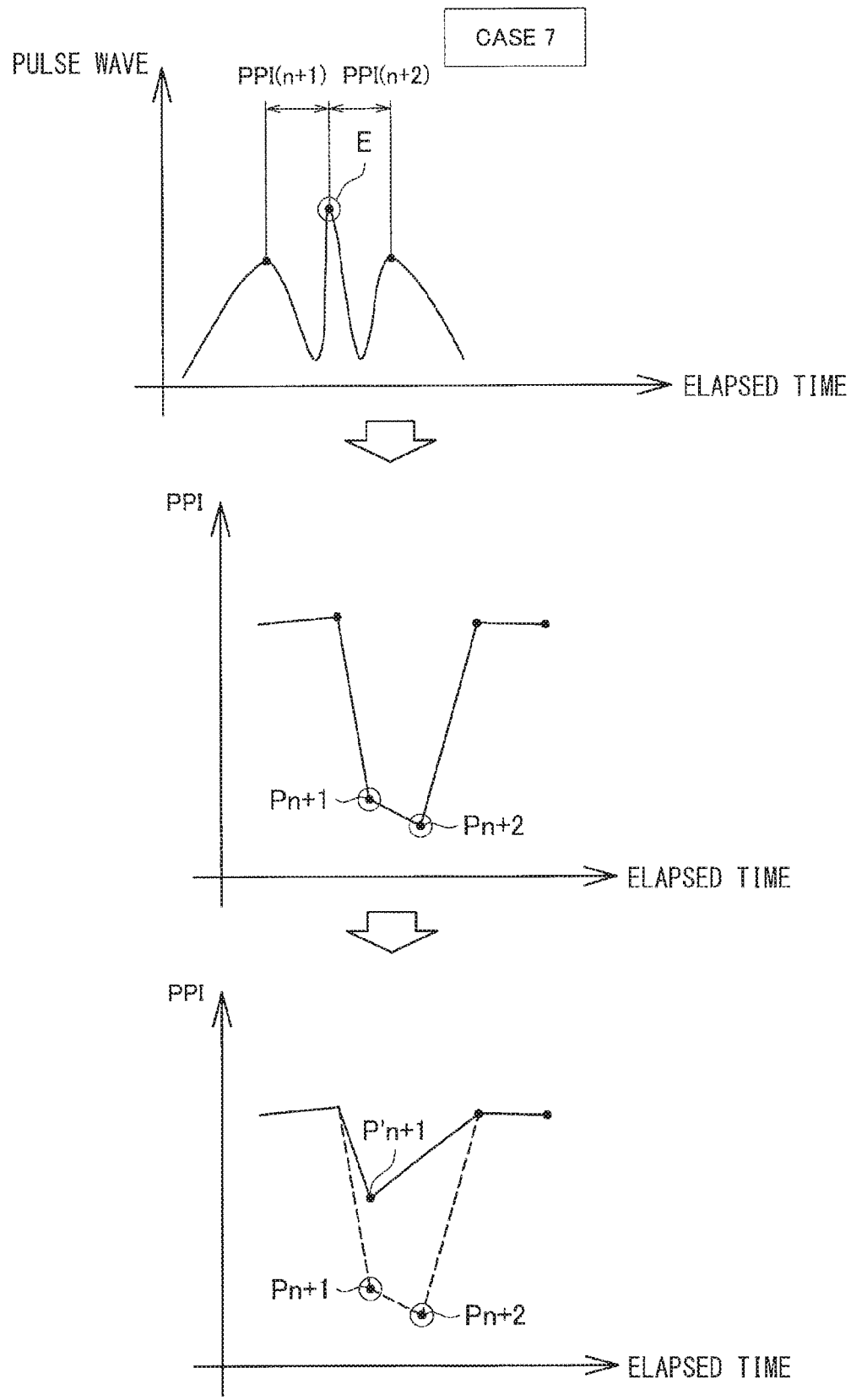

[ FIG. 20 ]
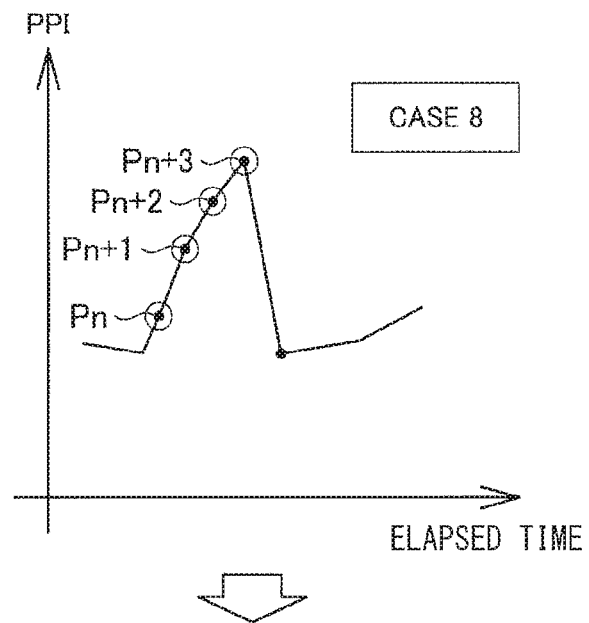
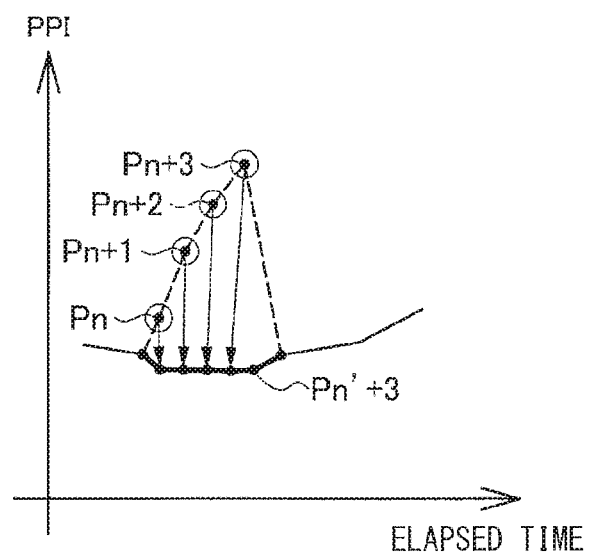

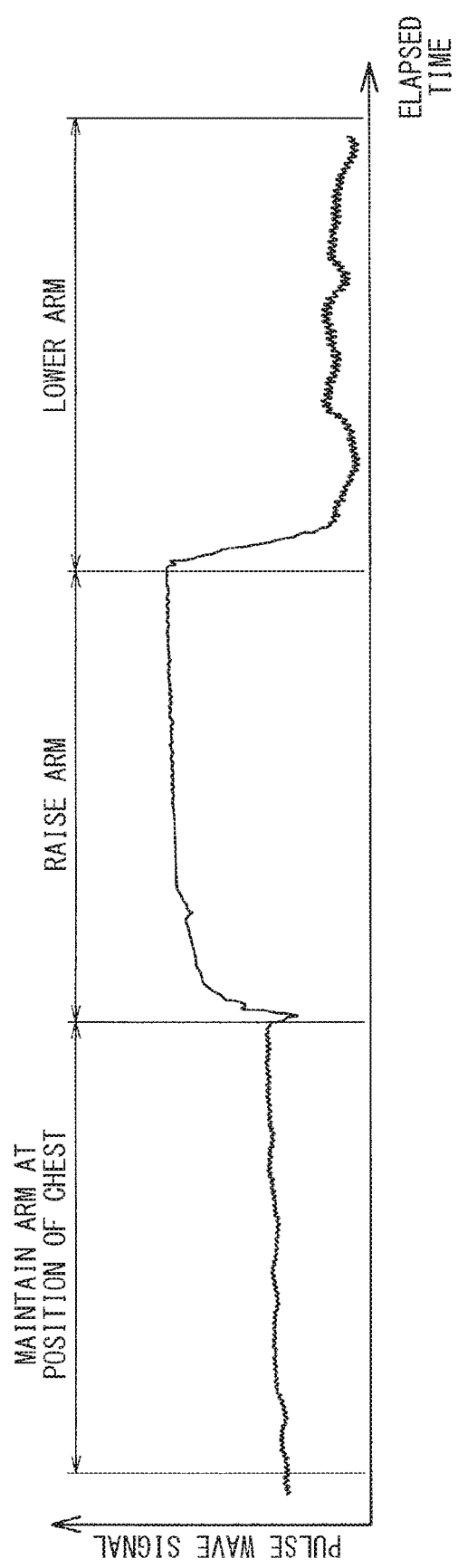
[FIG. 21]

[FIG. 22]
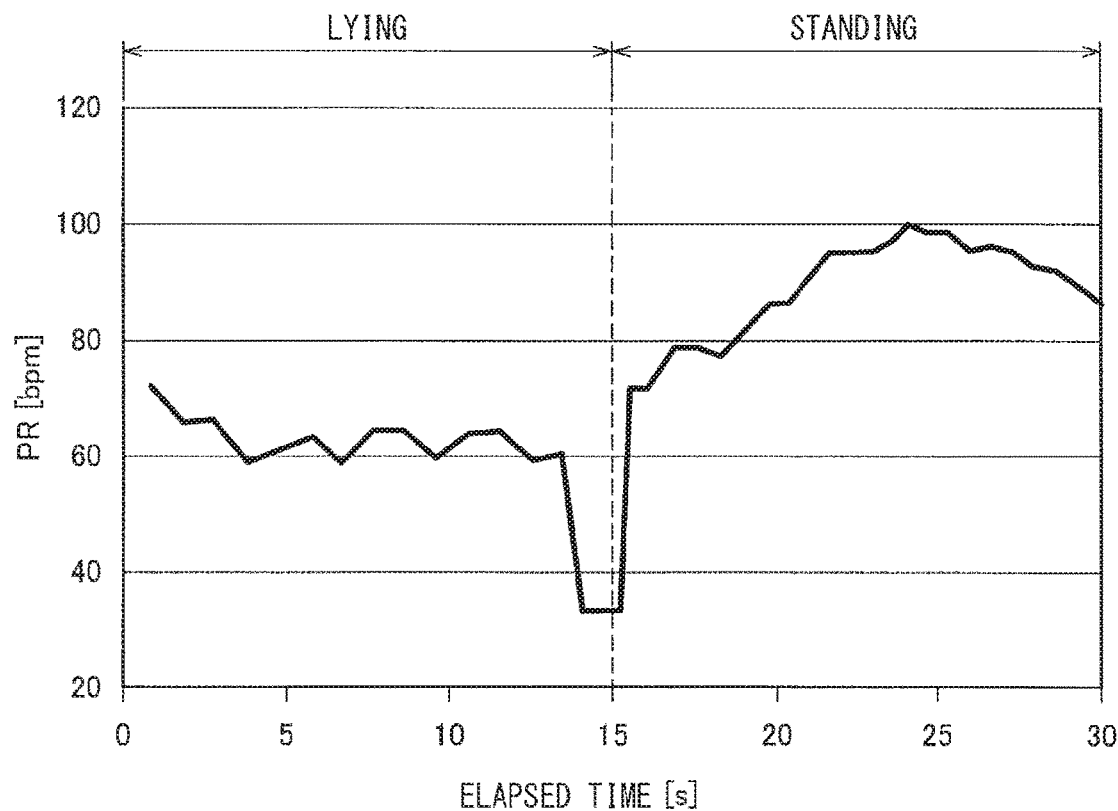
[FIG. 23]
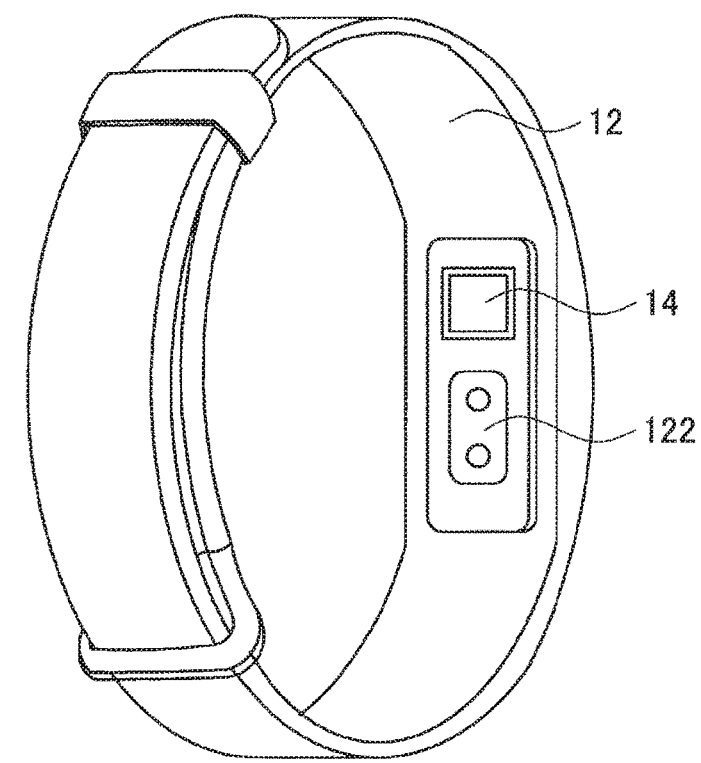

[ FIG. 24 ]
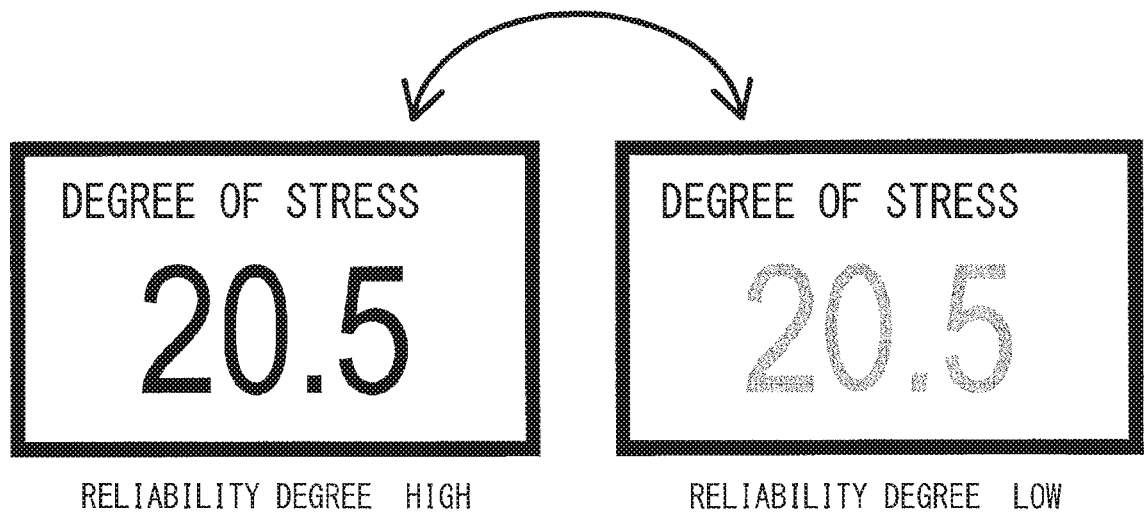
[ FIG. 25 ]
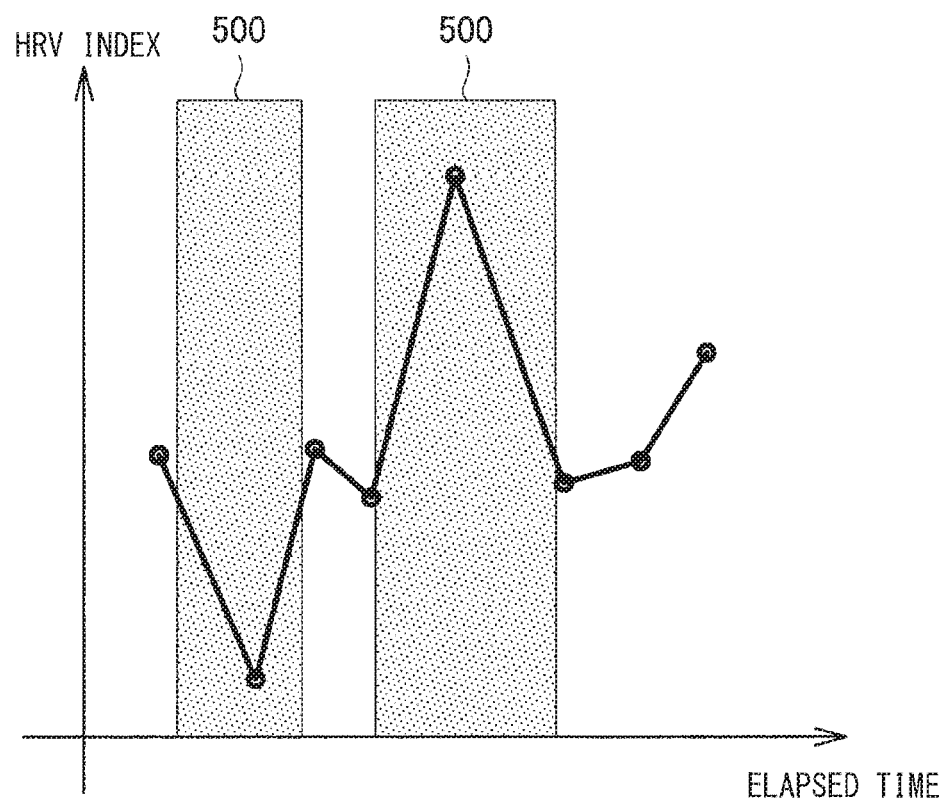

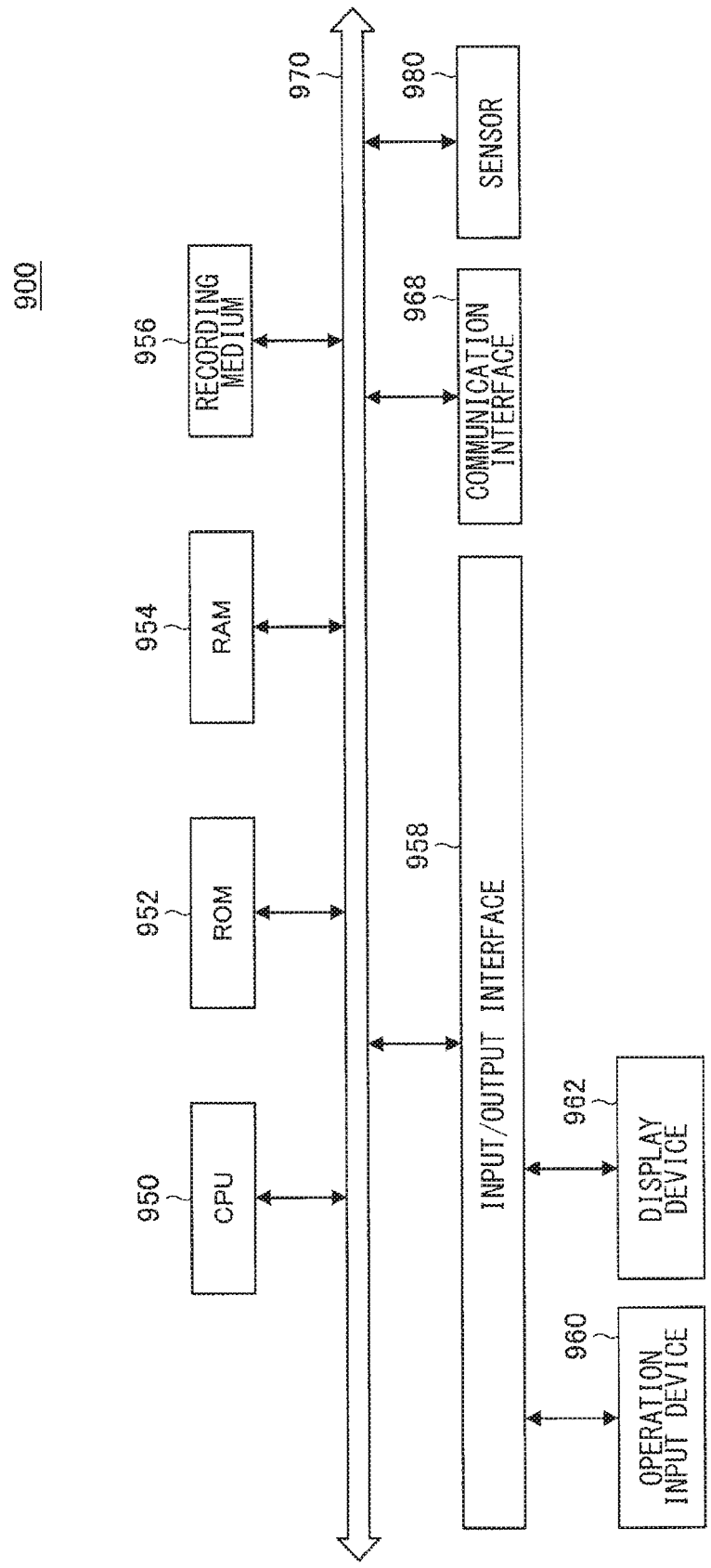
[FIG. 26]

INFORMATION PROCESSING APPARATUS, AND INFORMATION PROCESSING METHOD

CROSS REFERENCE TO RELATED APPLICATIONS

This application is a U.S. National Phase of International Patent Application No. PCT/JP2018/014438 filed on Apr. 4, 2018, which claims priority benefit of Japanese Patent Application No. JP 2017-125779 filed in the Japan Patent Office on Jun. 28, 2017. Each of the above-referenced applications is hereby incorporated herein by reference in its entirety.

TECHNICAL FIELD

The present disclosure relates to an information processing apparatus, an information processing method, and a program.

BACKGROUND ART

It is known to use HRV (Heart Rate Variability) indices based on heart rate variability when assessing the degree of psychological stress and assessing the autonomic nervous function. The HRV indices are acquirable, for example, from heart rate intervals (also referred to as R-R intervals (RRIs)) calculated by using electrocardiograms (ECGs) obtained by attaching electrodes or the like to portions of the bodies of users for measurement. The HRV indices are also acquirable from pulse rate intervals (PPIs) calculated from pulse rate variability that is highly correlated with heart rate variability. Apparatuses that acquire such RRIs and the like are disclosed in PTL 1 to 3 below.

CITATION LIST

Patent Literature

PTL 1: Japanese Unexamined Patent Application Publication No. H7-284482
PTL 2: Japanese Unexamined Patent Application Publication No. 2010-162282
PTL 3: Japanese Unexamined Patent Application Publication No. 2009-261419

SUMMARY OF THE INVENTION

Problems to be Solved by the Invention

In recent years, sensors and the like that detect heart rate variability and pulse rate variability have been miniaturized, which allows users to wear the sensors and constantly measure the heart rate variability and the pulse rate variability. As a result, the measurement is performed even in a state in which a user is freely moving such as doing daily actions (freely moving around), and the user is not sometimes in a resting state or does not maintain the same posture when the heart rate variability or the pulse rate variability is measured. In other words, the measurement of heart rate variability and pulse rate variability is not always in a preferable state. Heart rate variability and pulse rate variability measured under such a state may include, for example, noise caused by the movement of a user. This sometimes causes the reliability of the measured heart rate variability and pulse rate variability, the reliability of the HRV index calculated on the basis of the measured heart rate variability and pulse rate variability, and the like to be lower. Even an HRV index or the like regarding a user who is able to freely move around is, however, required to be an index having high reliability.

Accordingly, the present disclosure proposes a novel and improved information processing apparatus, information processing method, and program that make it possible to bring the measurement of the heart rate variability or pulse rate variability of a user freely moving around into a preferable state.

Means for Solving the Problems

According to the present disclosure, there is provided an information processing apparatus including: a reliability degree calculation section that calculates a reliability degree of pulsation variability data or a body index; and a control unit that controls various kinds of processing on the basis of the calculated reliability degree. The pulsation variability data is acquired from sensing data acquired by a pulse wave sensor worn by a user. The body index is calculated from the pulsation variability data and indicates a physical state of the user.

In addition, according to the present disclosure, there is provided an information processing method including: calculating a reliability degree of pulsation variability data or a body index; and controlling various kinds of processing on the basis of the calculated reliability degree. The pulsation variability data is acquired from sensing data acquired by a pulse wave sensor worn by a user. The body index is calculated from the pulsation variability data and indicates a physical state of the user.

Further, according to the present disclosure, there is provided a program for causing a computer to implement: a function of calculating a reliability degree of pulsation variability data or a body index; and a function of controlling various kinds of processing on the basis of the calculated reliability degree. The pulsation variability data is acquired from sensing data acquired by a pulse wave sensor worn by a user. The body index is calculated from the pulsation variability data and indicates a physical state of the user.

Effects of the Invention

As described above, according to the present disclosure, it is possible to provide an information processing apparatus, information processing method, and program that make it possible to bring the measurement of heart rate variability or pulse rate variability of a user freely moving around into a preferable state.

It should be noted that the effects described above are not necessarily limitative. Any of the effects indicated in this description or other effects that may be understood from this description may be attained in addition to the effects described above or in place of the effects described above.

BRIEF DESCRIPTION OF DRAWING

FIG. 1 is an explanatory diagram describing a configuration example of an information processing system 1 according to an embodiment of the present disclosure.
FIG. 2 is a block diagram illustrating a configuration of a wearable device 10 according to the embodiment.
FIG. 3 is an explanatory diagram describing a PPG sensor section 122 according to the embodiment.

FIG. 4 is an explanatory diagram illustrating an example of a pulse wave signal acquired by the PPG sensor section 122 according to the embodiment.

FIG. 5 is an explanatory diagram illustrating an example of time series data of PPIs acquired by the PPG sensor section 122 according to the embodiment.

FIG. 6 is an explanatory diagram illustrating an example in which the wearable device 10 according to the embodiment is worn.

FIG. 7 is a block diagram illustrating a configuration of a server 30 according to the embodiment.

FIG. 8 is a block diagram illustrating a configuration of a control unit 330 according to the embodiment.

FIG. 9 is an explanatory diagram illustrating a data flow according to the embodiment.

FIG. 10 is an explanatory diagram (Part 1) illustrating an example of a classified expression pattern of abnormal values according to the embodiment.

FIG. 11 is an explanatory diagram (Part 2) illustrating an example of a classified expression pattern of abnormal values according to the embodiment.

FIG. 12 is an explanatory diagram describing correction of an abnormal value according to a first method of the embodiment.

FIG. 13 is an explanatory diagram (Part 1) describing correction of an abnormal value according to a second method of the embodiment.

FIG. 14 is an explanatory diagram (Part 2) describing correction of an abnormal value according to the second method of the embodiment.

FIG. 15 is an explanatory diagram (Part 3) describing correction of an abnormal value according to the second method of the embodiment.

FIG. 16 is an explanatory diagram (Part 4) describing correction of an abnormal value according to the second method of the embodiment.

FIG. 17 is an explanatory diagram (Part 5) describing correction of an abnormal value according to the second method of the embodiment.

FIG. 18 is an explanatory diagram (Part 6) describing correction of an abnormal value according to the second method of the embodiment.

FIG. 19 is an explanatory diagram (Part 7) describing correction of an abnormal value according to the second method of the embodiment.

FIG. 20 is an explanatory diagram (Part 8) describing correction of an abnormal value according to the second method of the embodiment.

FIG. 21 is an explanatory diagram describing calculation of a reliability degree according to a second method of the embodiment.

FIG. 22 is an explanatory diagram describing calculation of a reliability degree according to a third method of the embodiment.

FIG. 23 is an explanatory diagram describing calculation of a reliability degree according to a fourth method of the embodiment.

FIG. 24 is an explanatory diagram (Part 1) describing output of a reliability degree according to a first method of the embodiment.

FIG. 25 is an explanatory diagram (Part 2) describing output of a reliability degree according to the first method of the embodiment.

FIG. 26 is an explanatory diagram describing an example of a hardware configuration of an information processing apparatus 900 according to the embodiment.

MODES FOR CARRYING OUT THE INVENTION

The following describes a preferred embodiment of the present disclosure in detail with reference to the accompanying drawings. It should be noted that, in this description and the accompanying drawings, components that have substantially the same functional configuration are indicated by the same reference signs, and thus redundant description thereof is omitted.

In addition, in this description and the drawings, a plurality of components that has substantially the same or similar functional configuration is sometimes distinguished from each other by attaching different numerals after the same reference numerals. However, when there is no need in particular to distinguish a plurality of components that has substantially the same or similar functional configuration, the same reference signs alone are attached. In addition, similar components of different embodiments are sometimes distinguished by attaching different alphabets to the same reference numerals. However, when there is no need in particular to distinguish similar components from each other, the same reference signs alone are attached.

It should be noted that the description is given in the following order.
1. Overview of Information Processing System 1 according to Present Embodiment
1.1 Overview of Information Processing System 1
1.2 Configuration of Wearable Device 10
1.3 Configuration of Server 30 according to Present Embodiment
2. Background of Creation of Embodiments according to the Present Disclosure
3. Detailed Configuration of Control Unit 330 according to Present Embodiment
4. Information Processing Method according to Present Embodiment
4.1 Detection of Abnormal Value
4.2 Regarding Parameter
4.3 Correction of Abnormal Value
4.4 Calculation of Reliability Degree
4.5 Output of Reliability Degree
5. Conclusion
6. Regarding Hardware Configuration
7. Supplement

1. OVERVIEW OF INFORMATION PROCESSING SYSTEM 1 ACCORDING TO PRESENT EMBODIMENT

<1.1 Overview of Information Processing System 1>

Next, a configuration according to an embodiment of the present disclosure is described. First, the configuration according to the embodiment of the present disclosure is described with reference to FIG. 1. FIG. 1 is an explanatory diagram describing a configuration example of an information processing system 1 according to the present embodiment.

As illustrated in FIG. 1, the information processing system 1 according to the present embodiment includes a wearable device 10, a server 30, and a user terminal 50, which are coupled to each other via a network 70 to make communication possible. Specifically, the wearable device 10, the server 30, and the user terminal (output unit) 50 are coupled to the network 70 via a base station or the like (e.g., a base station of a mobile phone, an access point of wireless LAN, or the like) that is not illustrated. It should be noted that, as a communication scheme used in the network 70, any scheme such as a wired or wireless scheme (e.g., WiFi (registered trademark), Bluetooth (registered trademark), or the like) is applicable, but it is preferable to use a communication scheme that allows a stable operation to be maintained.

(Wearable Device 10)

The wearable device 10 is able to be a device that is wearable on a portion of the body (such as an earlobe, the neck, an arm, a wrist, or an ankle) of a user, or an implant device (implant terminal) inserted into the body of the user. More specifically, it is possible to adopt, as the wearable device 10, various wearable devices of an HMD (Head Mounted Display) type, an ear device type, an anklet type, a bracelet type, a collar type, an eyewear type, a pad type, a batch type, a clothing type, and the like. Further, the wearable device 10 has sensors built therein, for example, such as a PPG (Photo Plethysmo Graphy) sensor section (pulse wave sensor) 122 that detects pulse wave signals (pulsation variability data) from pulses of a user, and a motion sensor section 124 that detects a motion state from a motion of a user (see FIG. 2). It should be noted that the details of the wearable device 10 are described below.

It should be noted that the following assumes that the wearable device 10 is provided with the PPG sensor section 122 (see FIG. 2). However, in the present embodiment, there may be provided, instead of the PPG sensor section 122, an ECG (Electrocardiogram) sensor (not illustrated) that detects an electrocardiogram of a user via electrodes (not illustrated) attached to the body of the user. In other words, it is possible in the embodiment described below to calculate an HRV (Heart Rate Variability) index by using pulse rate intervals (PPIs) that are acquirable from pulse wave signals, or R-R intervals (RRIs) that are acquirable from the electrocardiogram and represent the pulsation intervals of the heart. The HRV (Heart Rate Variability) index is a body index indicating the state of the body of a user.

(Server 30)

The server 30 includes, for example, a computer and the like. The server 30 processes the information acquired by the wearable device 10, and transmits the information acquired through the processing to another device (e.g., user terminal 50). It should be noted that the details of the server 30 are described below.

(User Terminal 50)

The user terminal 50 is a terminal for presenting, to a user, information (e.g., time series data of PPIs, an HRV index, reliability degree to be described below, and the like) provided in accordance with the present embodiment. For example, the user terminal 50 is able to be a tablet PC (Personal Computer), a smartphone, a mobile phone, a laptop PC, a notebook PC, an HMD, or the like.

It should be noted that FIG. 1 illustrates that the information processing system 1 according to the present embodiment includes the one wearable device 10 and user terminal 50, but the present embodiment is not limited thereto. For example, the information processing system 1 according to the present embodiment may include the plurality of wearable devices 10 and user terminals 50. Further, the information processing system 1 according to the present embodiment may include, for example, another communication device or the like that serves like a relay device in transmitting information from the wearable device 10 to the server 30. In addition, in the present embodiment, the wearable device 10 may be used as a stand-alone device. In this case, at least a portion of the functions of the server 30 and the user terminal 50 is performed in the wearable device 10.

<1.2 Configuration of Wearable Device 10>

Next, the configuration of the wearable device 10 according to the embodiment of the present disclosure is described with reference to FIGS. 2 to 6. FIG. 2 is a block diagram illustrating the configuration of the wearable device 10 according to the present embodiment. FIG. 3 is an explanatory diagram describing the PPG sensor section 122 according to the present embodiment. FIG. 4 is an explanatory diagram illustrating an example of a pulse wave signal acquired by the PPG sensor section 122 according to the present embodiment. FIG. 5 is an explanatory diagram illustrating an example of time series data of PPIs acquired by the PPG sensor section 122 according to the present embodiment. FIG. 6 is an explanatory diagram illustrating an example in which the wearable device 10 according to the present embodiment is worn.

As illustrated in FIG. 2, the wearable device 10 mainly includes an input unit 100, an output unit 110, a sensor unit 120, a control unit 130, a communication unit 140, and a storage unit 150. The following describes the respective functional units of the wearable device 10 in detail.

(Input Unit 100)

The input unit 100 receives the input of data or a command to the wearable device 10. More specifically, the input unit 100 is achieved by a touch panel, a button, a microphone, a drive, or the like.

(Output Unit 110)

The output unit 110 is a device for presenting information to a user, and outputs various kinds of information to the user as an image, sound, light, vibration, or the like, for example. The output unit 110 is achieved by a display, a speaker, an earphone, a light emitting element (e.g., light Emitting Diode (LED)), a vibrating module, or the like. It should be noted that the function of the output unit 110 may be provided by the user terminal 50 described below.

(Sensor Unit 120)

The sensor unit 120 is provided in the wearable device 10 worn on the body of a user, and includes the PPG sensor section 122 that detects pulse wave signals of the user. In addition, the sensor unit 120 may include the motion sensor section 124 for detecting the motion state of a user. The following describes the PPG sensor section 122 and the motion sensor section 124 included in the sensor unit 120.

—PPG Sensor Section 122—

The PPG sensor section 122 is worn on a portion of the body of a user such as skin (e.g., earlobe, neck, both arms, wrist, ankle, or the like) to detect pulse wave signals of the user. Here, a pulse wave signal is a waveform of the pulsation of an artery that appears on the body surface or the like due to a change in pressure on the inner wall of the artery. The change is made by blood being sent to the entire body through the artery because of contraction of a muscle of the heart with a constant rhythm (pulsation, and it should be noted that the number of times the heart pulses within unit time is referred to as heart rate). To acquire pulse wave signals, the PPG sensor section 122 irradiates a blood vessel 202 in a measurement site 200 such as a hand, an arm, the neck, or a leg of a user with light as illustrated in FIG. 3, and detects a substance moving in the blood vessel of the user or light scattered by a living tissue that remains still. The radiated light is absorbed by the red blood cells in the blood vessel 202. Accordingly, the amount of absorbed light is proportional to the amount of blood flowing into the blood vessel 202 in the measurement site 200. Therefore, detecting the intensity of the scattered light allows a change in the amount of flowing blood to be known. Further, a change in the amount of bloodstream allows the waveform of the pulsation of the artery causing the change in the amount of bloodstream to be detected. In other words, the change in the amount of bloodstream allows the pulse wave signals to be detected. It should be noted that such a method is referred to as photoplethysmography (PPG) method.

Specifically, the PPG sensor section 122 has a small laser (not illustrated) built therein. The small laser is able to radiate coherent light. The PPG sensor section 122 radiates light having a predetermined wavelength of about 850 nm, for example. It should be noted that it is possible in the present embodiment to select the wavelength of the light radiated by the PPG sensor section 122 as appropriate. Further, the PPG sensor section 122 has, for example, a photo diode (Photo Detector: PD) built therein, and converts the intensity of detected light into an electric signal, thereby acquiring a pulse wave signal. It should be noted that the PPG sensor section 122 may have a CCD (Charge Coupled Devices) sensor, a CMOS (Complementary Metal Oxide Semiconductor) sensor, or the like built therein instead of the PD. In addition, one or more PD or the like as described above may be provided in the PPG sensor section 122.

It should be noted that the present embodiment is not limited to the acquisition of a pulse wave signal using the PPG method described above, but a pulse wave signal may be acquired in another method. For example, in the present embodiment, a pulse wave signal may be acquired in a laser Doppler method. The laser Doppler method is a method using a frequency shift caused, due to the Doppler effects of bloodstream, by light scattered by a scattering substance (mainly red blood cell) moving in the blood vessel 202 of a user when the measurement site 200 of the user is irradiated with laser light. In addition, in the present embodiment, a pulse wave signal may be detected by using a dynamic light scattering (DLS) method. The DLS method is a method using interference light caused, due to the Doppler effects, by light scattered by a scattering substance moving in the blood vessel 202 when laser light is radiated, similarly to the above.

The PPG sensor section 122 is then able to detect pulse wave signals as time series data having a plurality of peaks as illustrated in FIG. 4. Here, as described with reference to FIG. 4, the peak intervals between a plurality of peaks appearing in pulse wave signals are referred to as pulse rate intervals (PPIs). It is possible to acquire PPIs by processing the pulse wave signals detected by the PPG sensor section 122. FIG. 5 illustrates an example of time series data of PPIs acquired in this manner. Although the value of each PPI varies with time as illustrated in FIG. 5, it is known that the PPIs are substantially normally distributed in a case where the state of the user is stable. Processing the time series data of PPIs as illustrated in FIG. 5 or the data group of PPI values makes it possible to calculate various HRV (Heart Rate Variability) indices serving as indices of the physical state of a user. It should be noted that the details of the various HRV indices are described below.

—Motion Sensor Section 124—

The motion sensor section 124 detects a change in acceleration caused by an action of a user, and detects the state of the user. A reliability degree is calculated on the basis of the detected state of the user as an index indicating whether the pulse wave signals at that time are appropriately measured. It should be noted that the details of the reliability degree are described below. For example, the motion sensor section 124 includes an acceleration sensor, a gyro sensor, a geomagnetic sensor, and the like.

In addition, the motion sensor section 124 may be an imaging device (not illustrated) that images a user by using an imaging element and various members such as a lens for controlling the formation of a subject image on the imaging device. In this case, an image shot by the imaging device described above captures an action or the like of a user. Further, the motion sensor section 124 may include an infra-red sensor, an ultrasonic sensor, or the like (not illustrated) that is able to recognize an action of a user. It should be noted that such an imaging device, infra-red sensor, and the like may be installed around a user as a device different from the wearable device 10.

Further, the motion sensor section 124 may include a positioning sensor (not illustrated). The positioning sensor is a sensor that detects the position of a user who is wearing the wearable device 10. Specifically, the positioning sensor is able to be a GNSS (Global Navigation Satellite System) receiver or the like. In this case, the positioning sensor is able to generate, on the basis of signals from a GNSS satellite, sensing data indicating the latitude/longitude of the current position of a user, and detect the movement (motion) of the user from a change in the sensing data. For example, it is possible to detect the relative positional relationship of a user from RFID (Radio Frequency Identification), an access point of Wi-Fi, information of a wireless base station, and the like. Accordingly, it is also possible to use such a communication device as the positioning sensor described above.

Further, the sensor unit 120 may include various biological sensors (not illustrated). The biological sensors are sensors that detect biological information indicating the state of a user. The biological sensors include, for example, one or more sensors that are worn directly or indirectly on a portion of the body of a user, and measure the brain waves, respiration, perspiration, myoelectric potential, skin temperature, skin electrical resistance, and the like of the user. In addition, the sensor unit 120 may include other various sensors such as a pressure sensor section 14 (see FIG. 23). Further, the sensor unit 120 may have a clock mechanism (not illustrated) built therein for grasping the accurate time, and associate the acquired pulse wave signals or the like with the time at which the pulse wave signals or the like are acquired. It should be noted that, in the present embodiment, the PPG sensor section 122 and the motion sensor section 124 that are two sensors of the sensor unit 120 may be provided to the different wearable devices 10. By doing so, it is possible to make the configuration of each wearable device 10 compact. This allows each wearable device 10 to be worn on various portions of the body of a user.

(Control Unit 130)

The control unit 130 is provided in the wearable device 10, and is able to control each block of the wearable device 10 and acquire time series data of PPIs from pulse wave signals outputted from the PPG sensor section 122 described above. The control unit 130 is achieved by hardware such as a CPU (Central Processing Unit), a ROM (Read Only Memory), and a RAM (Random Access Memory), for example. It should be noted that the function of the control unit 130 may be provided by the server 30 or the user terminal 50 described below.

(Communication Unit 140)

The communication unit 140 is provided in the wearable device 10, and is able to transmit and receive information to and from an external device such as the server 30 or the user terminal 50. In other words, it is possible to regard the communication unit 140 as a communication interface having functions of transmitting and receiving data. It should be noted that the communication unit 140 is achieved by a communication device such as a communication antenna, a transmission/reception circuit, or a port.

(Storage Unit 150)

The storage unit 150 is provided in the wearable device 10, and stores a program, information, and the like for the control unit 130 described above to execute various kinds of processing, and information acquired through the processing. It should be noted that the storage unit 150 is achieved, for example, by a nonvolatile memory such as a flash memory.

As described above, it is possible to adopt, as the wearable device 10, various wearable devices of an eyewear type, an ear device type, a bracelet type, an HMD type, and the like. FIG. 6 illustrates an example of the appearance of the wearable device 10. The wearable device 10 illustrated in FIG. 6 is a wristwatch type wearable device that is worn on a wrist of a user.

<1.3 Configuration of Server 30 According to Present Embodiment>

Next, the configuration of the server 30 according to the embodiment of the present disclosure is described with reference to FIG. 7. FIG. 7 is a block diagram illustrating the configuration of the server 30 according to the present embodiment. As described above, the server 30 includes, for example, a computer and the like. As illustrated in FIG. 7, the server 30 mainly includes an input unit 300, an output unit 310, a control unit 330, a communication unit 340, and a storage unit 350. The following describes the respective functional units of the server 30 in detail.

(Input Unit 300)

The input unit 300 receives the input of data or a command to the server 30. More specifically, the input unit 300 is achieved by a touch panel, a keyboard, or the like.

(Output Unit 310)

The output unit 310 includes, for example, a display, a speaker, a video output terminal, an audio output terminal, and the like, and outputs various kinds of information as an image, sound, and the like.

(Control Unit 330)

The control unit 330 is provided in the server 30, and is able to control each block of the server 30. Specifically, the control unit 330 controls various kinds of processing such as detection processing of detecting an abnormal value from pulse wave signals (pulsation variability data), correction processing of correcting pulse wave signals, and calculation processing of calculating an HRV index (body index) from pulse wave signals. The detection processing, the correction processing, and the calculation processing are performed in the server 30. The control unit 330 is achieved by hardware such as a CPU, a ROM, and a RAM, for example. It should be noted that the control unit 330 may execute a portion of the functions of the control unit 130 of the wearable device 10. In addition, the details of the control unit 330 are described below.

(Communication Unit 340)

The communication unit 340 is provided in the server 30, and is able to transmit and receive information to and from an external device such as the wearable device 10 or the user terminal 50. It should be noted that he communication unit 340 is achieved by a communication device such as a communication antenna, a transmission/reception circuit, or a port.

(Storage Unit 350)

The storage unit 350 is provided in the server 30, and stores a program and the like for the control unit 330 described above to execute various kinds of processing, and information acquired through the processing. More specifically, the storage unit 350 is able to store a database (DB) 352 (see FIG. 8) or the like including time series data of PPIs and the like acquired from the wearable devices 10 worn by a plurality of users. It should be noted that the storage unit 350 is achieved, for example, by a magnetic recording medium such as a hard disk (HD), a nonvolatile memory, or the like.

2. TECHNICAL BACKGROUND OF EMBODIMENT ACCORDING TO THE PRESENT DISCLOSURE

The overviews of the information processing system 1 according to the embodiment of the present disclosure, and the wearable device 10 and the server 30 included in the information processing system 1 have been described above. Next, before the details of the embodiment according to the present disclosure are described, the technical background of the embodiment according to the present disclosure is described.

As described above, the HRV index used in assessing the degree of psychological stress and assessing the autonomic nervous function is acquirable from RRIs calculated, for example, on the basis of heart rate variability (electrocardiogram). Further, the HRV indices are acquirable from PPIs calculated from pulse rate variability that is highly correlated with heart rate variability. Such heart rate variability and pulse rate variability are influenced by not only a change in the autonomic nervous system of a user, but also a change in the physical state of the user. Accordingly, it is desirable that the user be in a resting state and maintains the same posture at the time of measurement.

Incidentally, in recent years, sensors and the like that detect heart rate variability and pulse rate variability have been miniaturized, which allows users to wear the sensors and constantly measure the heart rate variability and the pulse rate variability. As a result, the measurement is performed even in a state in which a user is freely moving such as doing daily actions (freely moving around), and the user is not in a resting state or does not maintain the same posture when the heart rate variability or the pulse rate variability is measured. Heart rate variability and pulse rate variability measured under such a state may include, for example, noise caused by the movement of a user. This sometimes causes the reliability of the measured heart rate variability and pulse rate variability, the reliability of the HRV index calculated on the basis of the measured heart rate variability and pulse rate variability, and the like to be lower.

Accordingly, in view of the circumstances described above, the present inventor has conceived calculating a reliability degree for the measurement of heart rate variability and pulse rate variability, presenting the calculated reliability degree to a user together with an HRV index, and guiding the state of the user to a state that is ideal for the measurement. For example, in a case where a low reliability degree is presented to a user from the information processing system 1 according to the embodiment of the present disclosure, the user is guided to actions of resting and maintaining the same posture to improve the reliability degree. As a result, the state of the user comes closer to the state that is ideal for measurement. This allows the measurement of the heart rate variability or pulse rate variability of the user to transition to a preferable state. Further, the present inventor has also conceived feeding back the calculated reliability degree to the control of the information processing system 1 described above, thereby preferably controlling the information processing system 1 such as accurately calculating an HRV index and suppressing the amount of battery consumption.

In other words, in the the present disclosure described below, there are proposed an information processing apparatus, information processing method, and program that make it possible to bring the measurement of heart rate variability or pulse rate variability of a user freely moving around into a preferable state.

In addition, data (pulse wave signals) of heart rate variability and pulse rate variability sometimes includes abnormal values (noise) due to, for example, the "body movement of a user," "body characteristics," "measurement device noise," "measurement algorithm mistakes," and the like. Calculating an HRV index by using the data of the heart rate variability and pulse rate variability data including such abnormal values sometimes causes the HRV index to deviate from the correct normal HRV index that should be calculated. Therefore, when calculating an HRV index, it is necessary to address the abnormal values described above to prevent the HRV index from deviating from the correct normal HRV index that should be calculated.

Accordingly, in view of the circumstances described above, the present inventor has conceived accurately detecting abnormal values (noise) from data of heart rate variability and pulse rate variability, and correcting the data of the heart rate variability and pulse rate variability on the basis of the detected abnormal values. By doing so, it is possible to prevent an HRV index to be calculated from deviating from the correct normal HRV index that should be calculated. In other words, the present disclosure described below proposes an information processing apparatus, information processing method, and program that make it possible to increase the accuracy of an HRV index calculated on the basis of data obtained by measuring heart rate variability or pulse rate variability. The following subsequently describes such embodiments of the present disclosure in detail.

3. DETAILED CONFIGURATION OF CONTROL UNIT 330 ACCORDING TO PRESENT EMBODIMENT

The following describes the configuration of the control unit 330 according to the present embodiment with reference to FIG. 8. FIG. 8 is a block diagram illustrating the configuration of the control unit 330 according to the present embodiment. As illustrated in FIG. 8, the control unit 330 mainly includes a detection section 332, a detection correction control section 334, a correction section 336, a reliability degree calculation section 338, and an HRV index calculation section 342. The following describes the respective functional sections of the control unit 330 in detail.
(Detection Section 332)

The detection section 332 detects an abnormal value from time series data of PPIs. Here, the abnormal value refers to a value greatly deviated from a statistical point of view in time series data of PPIs or a data group of PPI values due to noise such as external impact. Further, the detection section 332 generates a data string in which a flag is assigned to the PPI value estimated to be an abnormal value in the time series data of PPIs, and outputs the data string to the correction section 336 described below. The flag indicates an abnormal value. For example, the detection section 332 assigns "1" to the PPI value estimated to be an abnormal value, and assigns "0" to the PPI value estimated to be a normal value. It should be noted that the detection of an abnormal value by the detection section 332 is described in detail below.
(Detection Correction Control Section 334)

The detection correction control section 334 corrects various parameters used for the detection of an abnormal value by the detection section 332 described above. For example, the detection correction control section 334 calculates the average value or the standard deviation from a data group of PPI values acquired from pulse wave signals of a user measured in the past, and updates the various parameters described above on the basis of the calculated average value and the like. By doing so, it is possible to detect abnormal values by using parameters preferable for the respective users. This makes it possible to increase the accuracy of the detection of an abnormal value. It should be noted that the above-described updating of parameters by the detection correction control section 334 may be performed periodically, or may be performed when a user selects to perform the updating. In addition, fixed values determined by conducting an experiment and an observation in advance may be used as the parameters described above. In this case, the detection correction control section 334 does not update the parameters. In addition, the details of the updating of various parameters by the detection correction control section 334 are described below.
(Correction Section 336)

The correction section 336 performs correction processing, such as interpolating or removing an abnormal value, on time series data of PPIs to which an abnormality flag is assigned. The time series data of PPIs is acquired from the detection section 332. The contents of the correction processing performed by the correction section 336 is selectable in accordance with the type of an HRV index calculated by the HRV index calculation section 342 described below. In addition, the correction section 336 may select the contents of the correction processing in accordance with the expression of the abnormal value described above. The time series data of PPIs corrected by the correction section 336 is outputted to the HRV index calculation section 342 described below. It should be noted that the details of the correction processing by the correction section 336 are described below.
(Reliability Degree Calculation Section 338)

The reliability degree calculation section 338 calculates the reliability degree of time series data of PPIs acquired from pulse wave signals or an HRV index acquired from the time series data of PPIs from the perspective of whether the state of a user is appropriate for the measurement of the pulse wave signals at the time of the measurement. Generally, in a case where HRV indices are calculated for assessing the degree of psychological stress and assessing the autonomic nervous function, it is considered desirable that a user be in a resting state and maintain the same posture at the time of the measurement of pulse wave signals. The pulse wave signals serve as the fundamental data of the HRV indices. This is because the pulse wave signals to be measure are influenced by not only a change in the autonomic nervous system of a user, but also a change in the physical state of the user. Therefore, if a user is in a resting state and maintains the same posture at the time of the measurement of pulse wave signals, the reliability degrees of time series data of PPIs and the HRV index become high. As the state of the user at the time of the measurement deviates more from the ideal state described above, the reliability degrees described above become lower. Therefore, the reliability degree calculation section 338 detects the state of a user at the time of the measurement of pulse wave signals, for example, on the basis of acceleration data of the motion sensor section 124 included in the wearable device 10, and calculates the reliability degrees on the basis of a result of the detection. The reliability degrees calculated in this manner by the reliability degree calculation section 338 are, for example, outputted to the user terminal 50 or the like, thereby being presented to a user. Alternatively, the reliability degrees are outputted to the wearable device 10 and used for the control of the wearable device 10. Further, the reliability degrees are outputted to another functional unit (e.g., HRV index calculation section 342 described below) of the server 30, and used for the control the processing in the other functional unit. It should be noted that the reliability degrees described above are also influenced by the wearing state of the PPG sensor section 122 at the time of the measurement of pulse wave signals. This makes possible calculation based on the wearing state described above. The details of the calculation of a reliability degree in the reliability degree calculation section 338 are described below.

(HRV Index Calculation Section 342)

The HRV index calculation section 342 calculates various HRV indices by using time series data of PPIs corrected by the correction section 336. The HRV index calculation section 342 calculates, for example, an RMSSD (Root Mean Square Successive Difference), an SDNN (Standard Deviation of the Normal to Normal Interval), LF/HF, and the like as the HRV indices. Further, these calculated HRV indices are further processed. This allows the further processed HRV indices to be used to assess the sleep state of a user, assess the degree of psychological stress of a user, assess the relaxation degree of a user, assess the concentration degree of a user, and the like. The HRV indices or the like calculated in this manner by the HRV index calculation section 342 are outputted to the user terminal 50 or the like, and presented to a user, for example.

For example, an RMSSD is the square root of the average value of the square of the difference between PPI values adjacent to each other in the time series. The RMSSD is thought to be an index indicating the tense state of the vagus nerve, which is one of the cranial nerves.

For example, an SDNN is the standard deviation of a data group of PPI values within a predetermined period (e.g., 120 seconds). The SDNN is thought to be an index indicating the activity state of the autonomic nervous system including both the sympathetic nerve and the parasympathetic nerve.

For example, LF/HF is the ratio of the power spectrum of the low frequency component (e.g., 0.004 to 0.15 Hz) to the power spectrum of the high frequency component (e.g., 0.15 to 0.4 Hz) of time series data of PPIs. LF/HF is thought to be an index indicating the balance between the sympathetic nerve and the parasympathetic nerve. High LF/HF is thought to indicate the state in which the sympathetic is predominant, and low LF/HF is thought to indicate the state in which the parasympathetic nerve is predominant.

4. INFORMATION PROCESSING METHOD ACCORDING TO PRESENT EMBODIMENT

The detailed configuration of the control unit 330 according to the present embodiment has been described above. Next, the overview of an information processing method according to the present embodiment is described with reference to FIG. 9. FIG. 9 is an explanatory diagram illustrating a data flow according to the present embodiment.

As illustrated in FIG. 9, pulse wave signals detected by the PPG sensor section 122 provided to the wearable device 10 are processed by the control unit 130 of the wearable device 10 (or the control unit 330 of the server 30 may be used), and time series data of PPIs is acquired. Further, the time series data of PPIs is processed by the detection section 332 of the server 30, and an abnormal value included in the time series data of PPIs is detected (detection of abnormal value). The correction section 336 then corrects the time series data of PPIs on the basis of the detected abnormal value, and outputs, to the HRV index calculation section 342, the time series data of PPIs whose abnormal value has been corrected (correction of abnormal value). At this time, the reliability degree calculation section 338 of the server 30 calculates a reliability degree by using acceleration data or the like of the motion sensor section 124 included in the wearable device 10 (calculation of reliability degree). Further, the HRV index calculation section 342 calculates an HRV index on the basis of the time series data of PPIs whose abnormal value has been corrected, and outputs the calculated HRV index to the user terminal 50 or the like together with the reliability degree (output of reliability degree). The following describes the details of processing at each stage of the information processing method according to the present embodiment.

<4.1 Detection of Abnormal Value>

In the detection of an abnormal value according to the present embodiment described below, successive PPI values in a period of a predetermined length are extracted from acquired time series data of PPIs, and an abnormal value is detected by comparing the extracted time series data of PPIs with the classified expression patterns of abnormal values. In other words, according to the present embodiment, it is not determined whether or not each PPI value included in the time series data of PPIs is an abnormal value, but a plurality of PPI values is determined at a time. This makes it possible to decrease processing and processing time for detecting an abnormal value.

With reference to FIGS. 10 and 11, the following describes an example of the detection of an abnormal value according to the present embodiment. Each of FIGS. 10 and 11 is an explanatory diagram illustrating an example of a classified expression pattern of abnormal values according to the present embodiment. FIGS. 10 and 11 illustrate eight expression patterns of abnormal values. The eight expression patterns are obtained by conducting an experiment and an observation in advance, extracting a period of a predetermined length of time series data of PPIs determined to include an abnormal value on the basis of a result of the observation, and classifying the behavior in the extracted period. Specifically, each expression pattern of abnormal values that has a period of a predetermined length includes five successive PPI values (indicated by black dots in the diagrams), and the PPI values determined to be abnormal values are further surrounded by circles in the diagrams. In the embodiment described below, an abnormal value is detected by determining, on the basis of the magnitude relation between numerical values, whether or not time series data of PPIs newly acquired applies to such expression patterns of abnormal values.

First, time series data of PPIs in a period of a predetermined length in which five PPI values from the head of the acquired time series data of PPIs are included is extracted. The following refers to the respective five PPI values included in the extracted time series data of PPIs as $p_n$, $p_{n+1}$, $p_{n+2}$, $p_{n+3}$, and $p_{n+4}$ in chronological order.

Next, in the detection of an abnormal value according to the present embodiment, the following expressions (1) to (5) are used to calculate respective parameters roc, $th_{roc1}$, $th_{roc2}$, $th_{eto1}$, and $th_{eto2}$ for detecting an abnormal value. It should be noted that $th_{roc1}$, $th_{roc2}$, $th_{eto1}$, and $th_{eto2}$ are calculated on the basis of an average value μ and a standard deviation σ obtained by statistically processing a plurality of pieces of time series data of PPIs obtained by measuring pulse wave signals in advance for various users a plurality of times, and an average value μ' and a standard deviation σ' obtained by statistically processing time series data of the difference values of PPI values adjacent to each other. In addition, the following defines $th_{roc1}$, $th_{roc2}$, $th_{eto1}$, and $th_{eto2}$ as fixed values determined in advance.

[Expression 1]

$$roc=(p_{n+2}-p_n)/p_n \quad \text{Expression (1)}$$

$$th_{roc}=(v'-\alpha*\sigma')/\mu' \quad \text{Expression (2)}$$

$$th_{roc2}=(\mu'+\alpha*\sigma')/\mu' \quad \text{Expression (3)}$$

$$th_{eto1}=(\mu-\alpha*\sigma)/\mu \quad \text{Expression (4)}$$

$$th_{eto2}=(\mu+\alpha*\sigma)/\mu \quad \text{Expression (5)}$$

It should be noted that α included in expressions (2) to (5) is a value determined in advance on the basis of an experiment, an observation, and the like. It is possible to set 1.0 as α, for example.

(Case 1)

In a case where the following expressions (6) and (7) are satisfied for $p_n$ and $p_{n+1}$ included in the extracted time series data of PPIs, it is determined that the extracted time series data of PPIs corresponds to the case 1 of FIG. 10. In this case, $p_{n+1}$ and $p_{n+2}$ are detected as abnormal values.

[Expression 2]

$$th_{eto2}<p_{n+1}/p_n \quad \text{Expression (6)}$$

$$roc<th_{roc1} \quad \text{Expression (7)}$$

(Case 2)

In a case where the following expressions (8) and (9) are satisfied for $p_n$ and $p_{n+1}$ included in the extracted time series data of PPIs, it is determined that the extracted time series data of PPIs corresponds to the case 2 of FIG. 10. In this case, $p_{n+1}$ is detected as an abnormal value.

[Expression 3]

$$th_{eto2}<p_{n+1}/p_n \quad \text{Expression (8)}$$

$$th_{roc1}<roc<th_{roc2} \quad \text{Expression (9)}$$

(Case 3)

In a case where the following expressions (10) and (11) are satisfied for $p_n$ and $p_{n+1}$ included in the extracted time series data of PPIs, it is determined that the extracted time series data of PPIs corresponds to the case 3 of FIG. 10. In this case, $p_{n+1}$ and $p_{n+2}$ are detected as abnormal values.

[Expression 4]

$$th_{eto2}<p_{n+1}/p_n \quad \text{Expression (10)}$$

$$th_{roc2}<roc \quad \text{Expression (11)}$$

(Case 5)

In a case where the following expressions (12) and (13) are satisfied for $p_n$ and $p_{n+1}$ included in the extracted time series data of PPIs, it is determined that the extracted time series data of PPIs corresponds to the case 5 of FIG. 11. In this case, $p_{n+1}$ and $p_{n+2}$ are detected as abnormal values.

[Expression 5]

$$th_{eto1}>p_{n+1}/p_n \quad \text{Expression (12)}$$

$$th_{roc2}<roc \quad \text{Expression (13)}$$

(Case 6)

In a case where the following expressions (14) and (15) are satisfied for $p_n$ and $p_{n+1}$ included in the extracted time series data of PPIs, it is determined that the extracted time series data of PPIs corresponds to the case 6 of FIG. 11. In this case, $p_{n+1}$ is detected as an abnormal value.

[Expression6]

$$th_{eto1}>p_{n+1}/p_n \quad \text{Expression (14)}$$

$$th_{roc1}<roc<th_{roc2} \quad \text{Expression (15)}$$

(Case 7)

In a case where the following expressions (16) and (17) are satisfied for $p_n$ and $p_{n+1}$ included in the extracted time series data of PPIs, it is determined that the extracted time series data of PPIs corresponds to the case 7 of FIG. 11. In this case, $p_{n+1}$ and $p_{+2}$ are detected as abnormal values.

[Expression 7]

$$th_{eto1}>p_{n+1}/p_n \quad \text{Expression (16)}$$

$$roc<th_{roc1} \quad \text{Expression (17)}$$

(Case 4)

Next, in a case where the extracted time series data of PPIs does not correspond to the cases 1 to 3 or cases 5 to 7 described above, but the following expressions (18) to (20) are satisfied for $p_n$, $p_{n+1}$, $p_{n+2}$, $p_{n+3}$, and $p_{n+4}$ included in the extracted time series data of PPIs, it is determined that the extracted time series data of PPIs corresponds to the case 4 of FIG. 10. In this case, $p_n$, $p_{n+1}$, $p_{n+2}$, and $p_{n+3}$ are detected as abnormal values.

[Expression 8]

$$th_{eto2}<p_{n+4}/p_{n+3} \quad \text{Expression (18)}$$

$$th_{eto1}<p_n/p_{n+3} \quad \text{Expression (19)}$$

$$p_n>p_{n+1}>p_{n+2}>p_{n+3} \quad \text{Expression (20)}$$

(Case 8)

In a case where the following expressions (21) to (23) are satisfied for $p_n$, $p_{n+1}$, $p_{n+2}$, $p_{n+3}$, and $p_{n+4}$ included in the extracted time series data of PPIs, it is determined that the extracted time series data of PPIs corresponds to the case 8 of FIG. 11. In this case, $p_n$, $p_{n+1}$, $p_{n+2}$, and $p_{n+3}$ are detected as abnormal values.

[Expression 9]

$$th_{eto2}>p_{n+4}/p_{n+3} \quad \text{Expression (21)}$$

$$th_{eto1}>p_n/p_{n+3} \quad \text{Expression (22)}$$

$$p_n<p_{n+1}<p_{n+2}<p_{n+3} \quad \text{Expression (23)}$$

A flag indicating an abnormal value is assigned to an abnormal value detected as described above. Further, time series data of PPIs in a period of a predetermined length in which the following five PPI values are included is extracted from the acquired time series data of PPIs, and the detection of an abnormal value as described above is performed. The detection of an abnormal value described above is then repeatedly performed until processing for the PPI value at the end point of the acquired time series data of PPIs is completed.

It should be noted that, in the detection of an abnormal value described above, it is determined to which of the eight expression patterns of abnormal values illustrated in FIGS. 10 and 11 the extracted time series data of PPIs in a period of a predetermined length corresponds, but the present embodiment is not limited to such a method. For example, in the present embodiment, an abnormal value may be detected by determining whether or not the extracted time series data of PPIs in a period of a predetermined length corresponds to not eight, but four of the expression patterns of abnormal values.

<4.2 Regarding Parameter>

In the detection of an abnormal value described above, it has been described that the respective parameters $th_{roc1}$, $th_{roc2}$, $th_{eto1}$, and $th_{eto2}$ used for detecting an abnormal value are defined as fixed values determined in advance. However, in the present embodiment, the respective parameters $th_{roc1}$, $th_{roc2}$, $th_{eto1}$, and $th_{eto2}$ are not limited to fixed values, but may be values that dynamically change.

Specifically, the tendencies of pulse wave signals of users differ in accordance with the physical characteristics of the users, and further change in accordance with the time of measurement, the age of the users, and the physical states of the users. Therefore, to accurately detect an abnormal value, it is preferable to use the parameters $th_{roc1}$, $th_{roc2}$, $th_{eto1}$, and $th_{eto2}$ in which the influence of the physical characteristics and the like of a user is reflected. Accordingly, in the present embodiment, when pulse wave signals of a user are newly measured, for example, the average values μ and μ' and the standard deviations σ and σ' are calculated by using time series data of PPIs (e.g., time series data of PPIs stored in a DB 352a in FIG. 8) acquired from the pulse wave signals of the user for one day before the measurement. Then, in the present embodiment, the parameters $th_{roc1}$, $th_{roc2}$ $th_{eto1}$, and $th_{eto2}$ are calculated by using expressions (2) to (5) described above on the basis of the calculated average values μ and μ' and standard deviations σ and σ', and the parameters $th_{roc1}$, $th_{roc2}$, $th_{eto1}$, and $th_{eto2}$ are used to detect an abnormal value. This is because it is possible to regard the time series data of PPIs acquired from the pulse wave signals of the user for one day as data in which the physical characteristics and physical state of the user are reflected. It should be noted that, to reflect the current physical state of the user, it is preferable to update the parameters $th_{roc1}$, $th_{roc2}$, $th_{eto1}$, and $th_{eto2}$ whenever pulse wave signals are newly measured, or periodically.

Further, when the average values μ and μ' and the standard deviations σ and σ' are calculated, time series data of PPIs in a section having a higher reliability degree described below may be used. In addition, when the average values μ and μ' and the standard deviations σ and σ' are calculated, time series data of PPIs used for the calculation may be weighted to more contribute to the average values μ and μ' and the standard deviations σ and σ' of the most recent time series data of PPIs. In addition, when the parameters $th_{roc1}$, $th_{roc2}$, $th_{eto1}$, and $th_{eto2}$ are calculated, α included in expressions (2) to (5) may be changed on the basis of sensing data acquired from various biological sensors (not illustrated) provided to the sensor unit 120 of the wearable device 10.

In other words, in the present embodiment, the calculation method of the parameters $th_{roc1}$, $th_{roc2}$, $th_{eto1}$, and $th_{eto2}$ is not particularly limited as long as the calculation method makes it possible to acquire the parameters $th_{roc1}$, $th_{roc2}$, $th_{eto1}$, and $th_{eto2}$ that allow an abnormal value to be accurately detected.

<4.3 Correction of Abnormal Value>

In the correction of an abnormal value according to the present embodiment described below, an abnormal value is detected from the acquired time series data of PPIs, and the time series data of PPIs is corrected on the basis of a result of the detection. According to the present embodiment, an abnormal value is corrected. This makes it possible to further increase the accuracy of various HRV indices acquired from the corrected time series data of PPIs. As the correction of an abnormal value, the following mainly describes two examples: a method of performing correction in accordance with the type of an HRV index; and a method of performing correction in accordance with the expression patterns of abnormal values described above.

(First Method)

First, with reference to FIG. 12, a first method of performing correction in accordance with the type of an HRV index is described as an example of the correction of an abnormal value. FIG. 12 is an explanatory diagram describing the correction of an abnormal value according to the first method of the present embodiment. Specifically, the upper portion of FIG. 12 illustrates a correction example of a case A where a section in which an abnormal value is detected is linearly complemented. The middle portion of FIG. 12 illustrates a correction example of a case B where an abnormal value is removed. The lower portion of FIG. 12 illustrates a correction example of a case C where no correction is performed. According to the first method, correction is performed in accordance with the type of an HRV index. This makes it possible to calculate an HRV index by using time series data of PPIs that is corrected in a preferable correction method, and further increase the accuracy of the calculated HRV index.

Specifically, in this method, in a case where an RMSSD is calculated as an HRV index, the case A illustrated in the upper portion of FIG. 12 is selected, and the section in which an abnormal value is detected is linearly complemented. In addition, in this method, in a case where an SDNN is calculated as an HRV index, the case B illustrated in the middle portion of FIG. 12 is selected, and an abnormal value is removed. Further, in this method, in a case where LF/HF is calculated as an HRV index, the case C illustrated in the lower portion of FIG. 12 is selected, and no correction is performed. In this case, when LF/HF is calculated, LF/HF is calculated by using the time series data of PPIs in the longest section having no successive abnormal values.

(Second Method)

Next, with reference to FIGS. 13 to 20, a second method of performing correction in accordance with an expression pattern of abnormal values is described as an example of the correction of an abnormal value. Each of FIGS. 13 to 20 is an explanatory diagram describing the correction of an abnormal value according to the second method of the present embodiment. In this method, a correction method is selected by taking into consideration occurrence reasons of expression patterns (cases 1 to 8) of abnormal values illustrated in FIGS. 10 and 11 generating. According to the second method, correction is performed in accordance with an expression pattern of abnormal values. This makes it possible to perform correction by taking into consideration an occurrence reason of an abnormal value. Therefore, it is possible to correct an abnormal value more preferably.

—Case 1—

First, with reference to FIG. 13, correction in the case 1 of an expression pattern of abnormal values is described. The case 1 is a case where a correct peak T that should be normally detected in the acquired pulse wave signals is not detected, but an erroneous peak E is detected as illustrated in the upper portion of FIG. 13, thereby acquiring time series data of PPIs as illustrated in the middle portion of FIG. 13. Specifically, in the time series data of PPIs illustrated in the middle portion of FIG. 13, the detection of the erroneous peak E causes $p_{n+1}$ to have a large value and causes $p_{n+2}$ to have a small value. In other words, $p_{n+1}$ and $p_{n+2}$ are abnormal values. The erroneous peak E is detected because a DC shift of pulse wave signals causes the erroneous peak E to occur near the position at which the correct peak T that should be normally detected should occur. In this case, it is inferred that, if the correct peak T is detected, normal $p_{n+1}$ has a smaller value than that of $p_{n+1}$ in the middle portion of FIG. 13, and normal $p_{n+2}$ has a larger value than that of $p_{n+2}$ illustrated in the middle portion of FIG. 13. Therefore, in the case 1, as illustrated in the lower portion of FIG. 13, $\Delta\beta$ is calculated in accordance with the following expression (24), and correction is performed to decrease, by $\Delta\beta$, $p_{n+1}$ that is an abnormal value and increase, by $\Delta\beta$, $p_{n+2}$ that is an abnormal value. In this manner, it is possible to correct an abnormal value caused by a DC shift.

[Expression 10]

$$\Delta\beta = p_{n+1} - \alpha P_n \qquad \text{Expression (24)}$$

It should be noted that $\alpha$ included in expression (24) is a value determined in advance on the basis of an experiment, an observation, and the like. It is possible to set 1.0 as $\alpha$, for example. In addition, $\alpha$ included in expression (22) may be $\alpha$ used when $\text{th}_{roc1}$, $\text{th}_{roc2}$, or the like is calculated.

—Case 2—

With reference to FIG. 14, correction in the case 2 of the expression pattern of abnormal values is described. The case 2 is a case where one peak T that should be normally detected in the acquired pulse wave signals is not detected, as illustrated in the upper portion of FIG. 14, thereby acquiring time series data of PPIs as illustrated in the middle portion of FIG. 14. Specifically, in the time series data of PPIs illustrated in the middle portion of FIG. 14, one peak T that should be normally detected is not detected, thereby causing two peaks to add up to the erroneous abnormal value $p_{n+1}$ though there should be normally two peaks. It is inferred that the abnormal value $p_{n+1}$ is caused by the influence of the arrhythmia of a user. Therefore, it is inferred that, if the correct peak T is detected, $p_{n+1}$ is divided into two in the time series data of PPIs. Accordingly, in the case 2, as illustrated in the lower portion of FIG. 14, correction is performed to insert $p'_{n+1}$ and $p''_{n+1}$ after $p_{n+1}$ that is an abnormal value, and divide $p_{n+1}$ into two. It is possible to calculate $p'_{n+1}$ and $p''_{n+1}$ on the basis of the following expressions (25) and (26). In this manner, it is possible to correct an abnormal value caused by the arrhythmia of a user.

[Expression 11]

$$p'_{n+1} = \alpha * p_{n+1} \qquad \text{Expression (25)}$$

$$p''_{n+1} = p_{n+1} - \alpha * p_{n+1} \qquad \text{Expression (26)}$$

It should be noted that $\alpha$ included in expressions (25) and (26) is a value determined in advance on the basis of an experiment, an observation, and the like. It is possible to set 0.5 as $\alpha$, for example.

—Case 3—

With reference to FIG. 15, correction in the case 3 of the expression pattern of abnormal values is described. The case 3 is a case where time series data of PPIs as illustrated in the middle portion of FIG. 15 is acquired because three peaks should be normally detected in the acquired pulse wave signals as illustrated in the upper portion of FIG. 15, but one large peak E causes failure in detecting two peaks T. Specifically, in this case, as illustrated in the upper portion of FIG. 15, an erroneous peak E caused by impact noise or the like is detected, and it is not possible to detect two correct peaks T that are positioned near the erroneous peak E and should be normally detected. As illustrated in the middle portion of FIG. 15, the abnormal values $p_{n+1}$ and $p_{n+2}$ having large values are detected. In this case, it is inferred that, if the correct peaks T are detected, the abnormal values $p_{n+1}$ and $p_{n+2}$ are divided into three. Therefore, in the case 3, as illustrated in the lower portion of FIG. 15, the abnormal value $p_{n+1}$ is decreased by $\Delta\beta_1$, the abnormal value $p_{n+2}$ is decreased by $\Delta\beta_2$, and $p'_{n+1}$ is inserted in the middle of the abnormal values $p_{n+1}$ and $p_{n+2}$. It is possible to calculate $p'_{n+1}$ in accordance with the following expression (27). It should be noted that it is possible to determine $\Delta\beta_1$ and $\Delta\beta_2$ from values or expressions defined in advance on the basis of experiments, observations, and the like. In this manner, it is possible to correct an abnormal value caused by impact noise or the like.

[Expression 12]

$$p'_{n+1} = \Delta\beta_1 + \Delta\beta_2 \qquad \text{Expression (27)}$$

—Case 4—

With reference to FIG. 16, correction in the case 4 of the expression pattern of abnormal values is described. In the case 4, as illustrated in the upper portion of FIG. 16, the PPI values in the time series data of PPIs are gradually lowered ($p_n$, $p_{n+1}$, $p_{n+2}$, and $p_{n+3}$), and return, at a certain time point, to the normal value ($p_{n+4}$) that should be detected. Such abnormal values $p_n$, $p_{n+1}$, $p_{n+2}$, and $p_{n+3}$ are generated by detecting peaks at intervals shorter than those of the normal pulse waves because of the detection of erroneous peaks generated by adding high-frequency noise caused by heartbeat to pulse wave signals. For example, in the PPG sensor section 122, a high-frequency noise of about 3 Hz is added to the pulse waves that are amplified with a period of about 1 Hz. In such a case, if correct peaks are detected, peaks that should be detected should be less than four peaks detected as abnormal values. Therefore, in the case 4, as illustrated in the lower portion of FIG. 16, the abnormal value $p_n$, $p_{n+1}$, and $p_{n+2}$ are corrected to m, and $p_{n+3}$ is deleted. It is possible to calculate m in accordance with the following expression (28). In this manner, it is possible to correct an abnormal value caused by high-frequency noise or the like.

[Expression 13]

$$m = (p_n + p_{n+1} + p_{n+2} + p_{n+3})/3 \qquad \text{Expression (28)}$$

—Case 5—

With reference to FIG. 17, correction in the case 5 of the expression pattern of abnormal values is described. Similarly to the case 1, the case 5 is a case where a correct peak T that should be normally detected in the acquired pulse wave signals is not detected, but an erroneous peak E is detected as illustrated in the upper portion of FIG. 17, thereby acquiring PPI time series data as illustrated in the middle portion of FIG. 17. Specifically, in the time series data of PPIs illustrated in the lower portion of FIG. 17, the detection of the erroneous peak E causes $p_{n+1}$ to have a small value and causes $p_{n+2}$ to have a large value. In other words, $p_{n+1}$ and $p_{n+2}$ are abnormal values. The erroneous peak E is detected because a DC shift of pulse wave signals causes the erroneous peak E to occur near the position at which the correct peak T that should be normally detected should occur. In this case, it is inferred that, if the correct peak T is detected, normal $p_{n+1}$ has a larger value than that of $p_{n+1}$ illustrated in the middle portion of FIG. 17, and normal $p_{n+2}$ has a smaller value than that of $p_{n+2}$ illustrated in the middle portion of FIG. 17. Therefore, in the case 5, as illustrated in the lower portion of FIG. 17, $\Delta\beta$ is calculated in accordance with the following expression (29), and correction is performed to increase, by $\Delta\beta$, $p_{n+1}$ that is an abnormal value and decrease, by $\Delta\beta$, $p_{n+2}$ that is an abnormal value. In this manner, it is possible to correct an abnormal value caused by a DC shift.

[Expression 14]

$$\Delta\beta = p_{n+1} - \alpha P_n \quad \quad \text{Expression (29)}$$

It should be noted that a included in expression (29) is a value determined in advance on the basis of an experiment, an observation, and the like. It is possible to set 1.0 as α, for example.

—Case 6—

With reference to FIG. 18, correction in the case 6 of the expression pattern of abnormal values is described. The case 6 is a case in which one peak should be normally detected in the acquired pulse wave signals as illustrated in the upper portion of FIG. 18, but time series data of PPIs as illustrated in the middle portion of FIG. 18 is acquired because an erroneous peak E due to impact noise or the like caused by external impact is also detected. In this case, it is estimated that, if a correct peak is detected, one peak is detected. Therefore, in the case 6, as illustrated in the lower portion of FIG. 18, $p_{n+1}$ is added to $p_{n+2}$ in accordance with the following expression (30) to calculate new $p'_{n+2}$. Then, in the case 6, $p_{n+2}$ is corrected to calculated $p'_{n+2}$, and $p_{n+1}$ is deleted. In this manner, it is possible to correct an abnormal value caused by impact noise or the like.

[Expression 15]

$$p'_{n+2} = p_{n+1} + p_{n+2} \quad \quad \text{Expression (30)}$$

—Case 7—

With reference to FIG. 19, correction in the case 7 of the expression pattern of abnormal values is described. The case 7 is a case in which one peak should be normally detected in the acquired pulse wave signals as illustrated in the upper portion of FIG. 19, but time series data of PPIs as illustrated in the middle portion of FIG. 19 is acquired because an erroneous peak E due to impact noise or the like caused by external impact is detected. In this case, it is estimated that, if the correct peak T is detected, one peak is detected. Therefore, in the case 7, as illustrated in the lower portion of FIG. 19, $p_{n+1}$ is added to $p_{n+2}$ in accordance with the following expression (31) to calculate new $p'_{n+1}$. Then, in the case 7, $p_{n+1}$ is corrected to calculated $p'_{n+1}$, and $p_{n+2}$ is deleted. In this manner, it is possible to correct an abnormal value caused by impact noise or the like.

[Expression 16]

$$p'_{n+1} = p_{n+1} + p_{n+2} \quad \quad \text{Expression (31)}$$

—Case 8—

With reference to FIG. 20, correction in the case 8 of the expression pattern of abnormal values is described. In the case 8, as illustrated in the upper portion of FIG. 20, the PPI values in the time series data of PPIs are gradually higher ($p_n$, $p_{n+1}$, $p_{n+2}$, and $p_{n+3}$), and return, at a certain time point, to the normal value ($p_{n+4}$) that should be detected. Such abnormal values $p_n$, $p_{n+1}$, $p_{n+2}$, and $p_{n+3}$ are generated because the addition of high-frequency noise caused by heartbeat to pulse wave signals causes failure in detecting peaks that should be normally detected. In such a case, if the correct peaks T are detected, peaks that should be detected should be more than four peaks detected as abnormal values. Therefore, in the case 8, as illustrated in the lower portion of FIG. 20, correction is performed to replace the abnormal values $p_n$, $p_{n+1}$, $p_{n+2}$, replace $p_{n+3}$ with m, and add $p'_{n+3}$ similarly having the value of m after $p_{n+3}$. It is possible to calculate m in accordance with the following expression (32). In this manner, it is possible to correct an abnormal value caused by high-frequency noise or the like.

[Expression 17]

$$m = (p_n + p_{n+1} + p_{n+2} + p_{n+3})/5 \quad \quad \text{Expression (32)}$$

It should be noted that, in the present embodiment, the correction of an abnormal value is not limited to the method described above, or is not particularly limited. In the present embodiment, for example, an abnormal value may be corrected in accordance with a reliability degree described below. Specifically, it is estimated in this case that an abnormal value detected in a section of time series data of PPIs having a higher reliability degree is generated by some change in the autonomic nervous system of a user, and it is selected not to actively correct the abnormal value. In contrast, it is estimated that an abnormal value detected in a section of time series data of PPIs having a lower reliability degree is generated by external influence such as impact, and it is selected to actively correct the abnormal value. Further, in the present embodiment, with respect to the detection of an abnormal value and the correction of an abnormal value, the tendencies of a user's past time series data of PPIs may be learned by machine learning, and an abnormal value may be detected and corrected in accordance with the tendencies of each user on the basis of a result of the learning.

<4.4 Calculation of Reliability Degree>

In the calculation of a reliability degree according to the present embodiment described below, the reliability degree of time series data of PPIs acquired from pulse wave signals or an HRV index acquired from the time series data of PPIs is calculated from the perspective of whether the state of a user is appropriate for the measurement of the pulse wave signals at the time of the measurement. As described above, in a case where HRV indices are calculated for assessing the degree of psychological stress and assessing the autonomic nervous function, it is desirable that a user be in a resting state and maintain the same posture at the time of the measurement of pulse wave signals. The pulse wave signals serve as the fundamental data of the HRV indices. In addition, it is also possible to calculate a reliability degree from the perspective of whether the wearing state of the PPG sensor section 122 that detects pulse wave signals is appropriate for the measurement of pulse wave signals. Therefore, in the present embodiment, calculating a reliability degree from the perspective described above and presenting the calculated reliability degree to a user allow the user to recognize the reliability of an HRV index that is presented together. In addition, in the present embodiment, it is also possible to control the sensor unit 120 of the wearable device 10, or control calculation processing of an HRV index on the basis of the calculated reliability degree. Various examples of the calculation of reliability degrees according to the present embodiment are described below.

(First Method)

First, as an example of calculation methods of a reliability degree $r_i$, a first method of calculating the reliability degree $r_i$ by using sensing data acquired by the motion sensor section 124 provided to the wearable device 10 is described. The sensing data acquired by the motion sensor section 124 is data in which an action of a user is reflected. Accordingly, an analysis of such data makes it possible to determine whether the user is in a state appropriate for the measurement of pulse wave signals.

Specifically, in this method, when pulse wave signals of a user are measured, acceleration data caused by an action of the user is acquired from the motion sensor section 124 worn by the user. Further, in this method, an acceleration norm is calculated from the acquired acceleration data at each sampling timing of pulse wave signals. Then, in this method, the plurality of calculated acceleration norms is averaged, for example, every other second, and a plurality of vectors Ai is acquired each of which has, as an element, an average value obtained by averaging the acceleration norms.

Next, in this method, the values of the plurality of vectors Ai are used to calculate an average value $\mu_i$ and a standard deviation $\sigma_i$. Further, in this method, the calculated average value $\mu_i$ and standard deviation a, are used to calculate a "resting score" Sr indicating the resting degree of a user and a "posture score" Sp indicating the degree of change in the posture of a user, that is, the motion state in accordance with the following expressions (33) and (34). It should be noted that it is estimated that Sr has a small value if a user is in the resting state, and Sp has a small value if there is no change in the posture of a user.

[Expression 18]

$$Sr=\mu_i/(2*3\ \sigma_\mu) \qquad \text{Expression (33)}$$

$$Sp=\sigma_i/(2*3\ \sigma_\sigma) \qquad \text{Expression (34)}$$

It should be noted that $\sigma_\mu$ and $\sigma_\sigma$ in expressions (33) and (34) described above are the respective standard deviations of a group of average values μi and a group of standard deviations σi calculated in advance from the plurality of vectors Ai acquired from acceleration data in daily life of various users.

It should be noted that it is preferable to perform clipping processing on the resting score Sr and the posture score Sp to cause the values thereof to fall within a range of 0 or more and 1 or less. Then, in this method, the reliability degree $r_i$ is calculated in accordance with the following expression (35) by using the calculated resting score Sr and posture score Sp.

[Expression 19]

$$r_i=\alpha*Sr+(1-\alpha)*Sp \qquad \text{Expression (35)}$$

It should be noted that a included in expression (33) is a value determined in advance on the basis of an experiment, an observation, and the like. It is possible to set a value greater than or equal to 0 and less than or equal to 1 as α, for example.

The reliability degree ri acquired in this manner is presented to a user, for example. In this case, the reliability degree ri may be presented to a user together with the calculated resting score Sr and posture score Sp.

In addition, in this method, it is sufficient if it is possible to calculate the resting score Sr indicating the resting degree of a user and the posture score Sp indicating the degree of change in the posture of a user, and a statistical value other than the average value $\mu_i$ and standard deviation $\sigma_i$ as described above may be used for calculation. Further, in this method, for example, the resting score Sr and the posture score Sp may be calculated by using acceleration data in the respective axial directions of the X, Y, and Z axes acquired from a triaxial acceleration sensor (not illustrated) built in the motion sensor section 124. In this case, the reliability degree ri in each axial direction may be obtained as described above by using the acceleration data in each axial direction, and the linear sum of the respective obtained reliability degrees ri may be used as the final reliability degree.

In addition, in this method, the posture and state of a user may be estimated from the sensing data acquired by the motion sensor section 124 using an existing algorithm, and the resting score Sr and the posture score Sp may be calculated on the basis of a result of the estimation. More specifically, on the basis of the sensing data acquired by the motion sensor section 124, it is estimated in which state of "sitting," "standing," "walking," "running," or the like a user is. Further, the state of a user is associated in advance with the value of the resting score Sr and the value of the posture score Sp (e.g., it is determined in advance that Sr is 1.0 in a case where the user is "sitting," Sr is 0.5 in a case where the user is in the "walking" state, and Sr is 0.0 in a case where the user is in the "running" state), the value of the resting score Sr and the value of the posture score Sp are selected on the basis of a result of the estimation described above, and the reliability degree ri is calculated by using the selected values. In addition, in this method, when pulse wave signals of a user are assumed, the state of the user may be estimated by using an existing algorithm from the sensing data acquired by the motion sensor section 124, and the resting score Sr may be the ratio of the longest posture time within the measurement period of the pulse wave signals.

(Second Method)

Next, as an example of calculation methods of the reliability degree $r_i$, a second method of calculating the reliability degree $r_i$ by using pulse wave signals acquired by the PPG sensor section 122 provided to the wearable device 10 is described with reference to FIG. 21. FIG. 21 is an explanatory diagram describing the calculation of a reliability degree according to the second method of the present embodiment. According to this method, it is possible to acquire the resting score Sr indicating the resting degree of a user without providing the motion sensor section 124.

Specifically, quantifying the variability in the direct-current components (DC components) included in the pulse wave signals in a predetermined period makes it possible to calculate the resting score Sr indicating the resting degree of a user. Therefore, in this method, a change in the direct-current components of the pulse wave signals is detected, the resting score Sr described above is calculated on the basis of a result of the detection, and the reliability degree $r_i$ is calculated by using the calculated resting score Sr similarly to the first method. More specifically, the pulse wave signals include pulsation components (AC components) corresponding to a change in the amount of bloodstream caused by the pulsation of the heart of a user, and direct-current components (DC components) corresponding to reflected light and scattered light from a blood layer other than the pulsation and a tissue other than blood. In a case where a user is in a non-resting state such as moving, a change in the amount of bloodstream caused by an action of the user or the detection of external light not coming from the PPG sensor section 122 caused because, for example, the PPG sensor section 122 is not correctly worn causes variability in the DC components of the pulse wave signals. For example, FIG. 21 illustrates the variability in pulse wave signals between a case the wearable device 10 is worn on an arm of a user or the PPG sensor section 122 is worn on the arm of the user, and the arm of the user is maintained at the chest height of the user, a case where the arm is raised above the chest, and a case where the arm is lowered below the chest. As can be seen from FIG. 21, raising and lowering the arm on which the PPG sensor section 122 is worn cause the variability in the DC components of the pulse wave signals as the variability in the height of the pulse wave signals in the diagram. In other words, if the posture of a user is maintained in a constant state, the DC components of pulse wave signals are maintained at a constant level. In this manner, it is possible to regard the DC components of pulse wave signals as an index in which the resting degree of a user is reflected. Accordingly, in this method, for example, it is possible to calculate variance ($\sigma^2$) by statistically processing the variability in the DC components of pulse wave signals in the measurement period of pulse wave signals, and use the inverse of the calculated variance as the resting score Sr described above.

(Third Method)

Next, as an example of the calculation methods of the reliability degree $r_i$, a third method of calculating the reliability degree $r_i$ by using a change in pulses based on pulse wave signals acquired by the PPG sensor section 122 provided to the wearable device 10 is described with reference to FIG. 22. FIG. 22 is an explanatory diagram describing the calculation of a reliability degree according to the third method of the present embodiment. According to this method, it is possible to acquire the posture score Sp indicating the degree of change in the posture of a user without providing the motion sensor section 124.

The pulse wave signals acquired by the PPG sensor section 122 are data in which a change caused by pulses of a user is reflected. Accordingly, an analysis of the pulse wave signals makes it possible to acquire the pulse rate of the user at predetermined time (e.g., pulse rate per minute, and it should be noted that the pulse rate is also referred to as beat per minute (bpm)). As the state of a user changes, the pulse rate accordingly changes. For example, as illustrated in FIG. 22, in a case where the state of a user changes from a lying state in which a user is lying to a standing state in which a user is standing, the pulse rate changes. More specifically, when lying, the pulse rate is stable at about 60 to 70 bpm. In a case of standing, the pulse rate changes to about 80 to 100 bpm. Therefore, it is possible to regard a change in the pulse rate as an index in which the degree of change in the posture of a user is reflected. Accordingly, in this method, for example, it is possible to calculate the variance ($\sigma^2$) by statistically processing the variability in the pulse rate in the measurement period of pulse wave signals, and use the inverse of the calculated variance as the posture score Sp described above. It should be noted that, in this method, the posture score Sp may be calculated by using the heart rate instead of the pulse rate.

(Fourth Method)

As described above, it is also possible to calculate the reliability degree $r_i$ from the perspective of whether the wearing state of the PPG sensor section 122 that detects pulse wave signals is appropriate for the measurement of pulse wave signals. Then, a fourth method of calculating the reliability degree $r_i$ on the basis of the wearing state of the PPG sensor section 122 is described as an example of the calculation methods of the reliability degree $r_i$ with reference to FIG. 23. FIG. 23 is an explanatory diagram describing the calculation of a reliability degree according to the fourth method of the present embodiment, and specifically illustrates the form of a wearable device 10a according to this method. According to this method, it is possible to calculate the reliability degree $r_i$ by taking into consideration the wearing state of the PPG sensor section 122.

To appropriately acquire pulse wave signals, the PPG sensor section 122 is required to be worn on a portion of the body of a user with appropriate tightness. Accordingly, in this method, as illustrated in FIG. 23, the pressure sensor section 14 is provided together with the PPG sensor section 122 inside a band portion 12 of the wristwatch type wearable device 10a. The pressure sensor section 14 detects the wearing state of the PPG sensor section 122. The pressure sensor section 14 makes it possible to detect pressure on the PPG sensor section 122 at the time of the measurement of pulse wave signals, and acquire the wearing state of the PPG sensor section 122 by using a result of the detection. The difference between the pressure on the ideally worn PPG sensor section 122 and the pressure detected by the pressure sensor section 14 within the pulse wave signal measurement period is then mathematically processed (e.g., variance ($\sigma^2$) is calculated) as an index indicating the wearing state of the PPG sensor section 122, and the reliability degree $r_i$ is calculated on the basis of a result of the processing in this method.

In addition, in this method, the wearing state of the PPG sensor section 122 is not limited to the detection by the pressure sensor section 14 described above, but may be detected by another sensor. For example, to appropriately acquire pulse wave signals, the PPG sensor section 122 is required to be in close contact with a portion of the body of a user. A temperature sensor section (not illustrated) may be then provided to a portion of the inside the band portion 12 of the wristwatch type wearable device 10a in close contact with the skin of a user. The temperature sensor section may detect the skin temperature of a user, and the wearing state of the PPG sensor section 122 may be detected by using a result of the detection.

(Fifth Method)

In addition, it is also possible to calculate the reliability degree $r_i$ by using the detection of an abnormal value described above. Then, a fifth method of calculating the reliability degree $r_i$ by using the detection of an abnormal value is described as an example of the calculation methods of the reliability degree $r_i$. In a case where an abnormal value is detected, it is estimated that a user is not in a state appropriate for the measurement of pulse wave signals or that the wearing state of the PPG sensor section 122 is not appropriate at the time of the measurement of pulse wave signals. In addition, in a case where no abnormal value is detected, it is estimated that a user is in a state appropriate for the measurement of pulse wave signals and that the wearing state of the PPG sensor section 122 is appropriate at the time of the measurement of pulse wave signals. Therefore, in this method, the reliability degree $r_i$ is calculated on the basis of the ratio of the period in which no abnormal value is detected within the measurement period of pulse wave signals of a user. Thus, according to this method, it is possible to calculate the reliability degree $r_i$ by taking into consideration the state of a user and the wearing state of the PPG sensor section 122.

It is possible to express the reliability degree $r_i$ in a certain measurement period by the following expression (36), for example, where $T_M$ represents the measurement time of time series data of PPIs in the measurement period, and $T_N$ represents the total time for which PPI values with no abnormal value detected in the measurement period are acquired.

[Expression 20]

$$r_i = T_N/T_M \quad \text{Expression (36)}$$

In addition, it is possible to express the reliability degree $r_i$ in a certain measurement period by the following expression (37), for example, where M represents the total number of pieces of data included in time series data of PPIs in the measurement period, and N represents the total number of pieces of data of PPI values with no abnormal value detected in the measurement period.

[Expression 21]

$$r_i = N/M \quad \text{Expression (37)}$$

In addition, in this method, the reliability degree $r_i$ may be calculated on the basis of the expression pattern of abnormal values in the acquired time series data of PPIs. For example, it is possible to express the reliability degree $r_i$ in a certain measurement period by the following expression (38), where M represents the total number of pieces of data included in time series data of PPIs in the measurement period, and $N_i$ represents the number of abnormal values in each case (i is a natural number from 1 to 8) that falls within the respective cases of the eight expression patterns of abnormal values described above and is determined as an abnormal value in the measurement period.

[Expression 22]

$$r_i = (\alpha_1 * N_1 + \alpha_2 * N_2 + \alpha_3 * N_3 + \alpha_4 * N_4 + \alpha_5 * N_5 + \alpha_6 * N_6 + \alpha_7 * N_7 + \alpha_8 * N_8)/M \quad \text{Expression (38)}$$

It should be noted that, in expression (38) described above, $\alpha i$ (i is a natural number from 1 to 8) represents a weighting factor determined for each of the cases of the expression patterns of abnormal values. It should be noted that it is possible to experimentally determine the weighting factor $\alpha i$, for example, on the basis of the time series data of PPIs measured in advance and environmental information (such as the presence or absence of external impact, the action patterns of a user, and the wearing state of the wearable device 10) at the time of the measurement. In addition, the weighting factor $\alpha i$ may be determined by weighting based on an expression reason of abnormal values for each expression pattern of abnormal values.

It should be noted that the calculation methods of the reliability degree $r_i$ described above are examples, and the calculation methods of the reliability degree $r_i$ according to the present embodiment are not limited to the methods described above. In addition, it is also possible to combine the calculation methods of the reliability degree $r_i$ described above with each other. In the present embodiment, for example, the reliability degree $r_i$ acquired in the fifth method described above may be integrated with the reliability degree $r_i$ calculated from the acceleration data acquired by the motion sensor section 124 in the first method described above to calculate the final reliability degree. Combining the calculation methods of the reliability degree $r_i$ described above in this manner makes it possible to further increase the accuracy of the reliability degree $r_i$.

<4.5 Output of Reliability Degree>

The reliability degree $r_i$ calculated as described above is, for example, presented to a user, thereby allowing the user to recognize the reliability of an HRV index presented together. In addition, for example, it is also possible to use the calculated reliability degree $r_i$ to control the sensor unit 120 of the wearable device 10, or control calculation processing of an HRV index. The following then describes various examples of output methods of the reliability degree $r_i$ according to the present embodiment.

(First Method)

First, a first method of presenting the reliability degree $r_i$ to a user is described with reference to FIGS. 24 and 25 as an example of the output methods of the reliability degree $r_i$. Each of FIGS. 24 and 25 is an explanatory diagram describing the output of the reliability degree $r_i$ according to the first method of the present embodiment. According to this method, for example, presenting the low reliability degree $r_i$ to a user guides the user to actions of resting and maintaining the same posture to improve the reliability degree $r_i$. In addition, in this method, in a case where the calculated reliability degree $r_i$ is lower than a predetermined value, the method may present, to a user, a reason therefor or an alert asking the user to improve the reliability degree $r_i$ on the assumption that the reliability of an HRV index or the like presented to the user is lower.

More specifically, in this method, as illustrated in FIG. 24, when the degree of stress calculated on the basis of an HRV index is displayed for a user, the display form of the degree of stress is changed in accordance with the reliability degree $r_i$. For example, as illustrated on the left portion of FIG. 24, in a case where the reliability degree $r_i$ is high, the degree of stress is displayed by increasing the contrast. Meanwhile, as illustrated on the right portion of FIG. 24, in a case where the reliability degree $r_i$ is low, the degree of stress is displayed by decreasing the contrast. Performing display by changing contrast in this manner facilitates a user to recognize the reliability of the displayed degree of stress. In addition, for example, as illustrated in FIG. 25, when time series data of HRV indices is graphically displayed for a user, gray-out display 500 is performed to make less noticeable time series data of HRV indices in a period in which the reliability degree $r_i$ is low. By doing so, the user pays attention to the HRV index that should come into focus, facilitating the user to confirm the HRV index.

As a method of presenting the reliability degree ri to a user, the color, luminance, and the like of the display of the reliability degree $r_i$ may be changed in accordance with the reliability degree $r_i$ for display. Numbers may be specifically used to display the reliability degree $r_i$. The method of presenting the reliability degree $r_i$ to a user is not particularly limited in this method. In this method, presenting the reliability degree $r_i$ to a user in this manner guides the user to actions of resting and maintaining the same posture to improve the reliability degree $r_i$. Further, a user is facilitated to recognize the reliability of the HRV index presented together with the reliability degree $r_i$.

In addition, in this method, when the reliability degree $r_i$ is presented, the reason why the reliability of the measurement of pulse wave signals decreases and the method of improving the reliability degree $r_i$ may be presented to a user. In this case, the cause of the decrease in the reliability degree $r_i$ is estimated with reference to the values or the like of the resting score Sr and the posture score Sp used to calculate the reliability degree $r_i$, and the reason for the decrease in the reliability degree $r_i$ and the method of improving the reliability degree $r_i$ are presented to a user on the basis of a result of the estimation. More specifically, in a case where an abrupt motion of a user is estimated as a cause of the decrease in the reliability degree $r_i$, an estimated reason is presented to the user like "the abrupt motion has decreased the reliability degree." In addition, in this method, a method of improving the reliability degree $r_i$ is presented to the user such as "Please rest" or "Please make a stable posture" in such a case. In addition, in a case where it is estimated as a cause of the decrease in the reliability degree $r_i$ that the wearing state of the PPG sensor section 122 is not favorable, a method of improving the wearing state of the PPG sensor section 122 is presented to a user such as "Please wear the wearable device again." Such presentation allows a user to recognize the reason why the reliability degree $r_i$ is low. This is more persuasive for the user than the presentation of the reliability degree $r_1$ alone to the user. Further, a user is facilitated to recognize a method of improving the reliability degree $r_i$ and guided to execute the method, making it possible to increase the accuracy of the measurement of pulse wave signals and even increase the accuracy of an HRV index.

It should be noted that, in this method, the reason why the reliability degree $r_i$ decreases and the method of presenting the method of improving the reliability degree $r_i$ are not limited to displaying characters such as words as described above. For example, the wearable device 10 may vibrate or an LED provided to the wearable device 10 may emit light on the basis of a pattern associated in advance with each reason, thereby presenting the reason to a user.

(Second Method)

Next, a second method of controlling the wearable device 10 by feeding back the reliability degree $r_i$ to the wearable device 10 is described as an example of the output methods of the reliability degree $r_i$. In this method, the operation of the PPG sensor section 122 that acquires pulse wave signals is temporarily stopped in a case where a period in which the reliability degree $r_i$ is lower than a predetermined value continues for a predetermined time (e.g., several seconds) or longer. For example, if the non-resting state continues because a user moves by running, the resting score Sr described above and the reliability degree $r_i$ calculated on the basis of the resting score Sr decrease. In a case where such a decrease in the reliability degree $r_i$ continues for a predetermined time or longer, it is estimated that the low reliability degree $r_i$ is maintained thereafter. The operation of the PPG sensor section 122 (e.g., light receiving operation) is temporarily stopped, and the acquisition of pulse wave signals is stopped. This is because, even if an HRV index is calculated on the basis of pulse wave signals in the state in which the reliability degree $r_i$ is low, it is not possible to acquire an index in which the state of a user is appropriately reflected. Further, stopping the operation of the PPG sensor section 122 allows the amount of battery consumption to be suppressed in the wearable device 10. In other words, according to this method, feeding back the reliability degree $r_i$ to the wearable device 10 makes it possible to bring the measurement operation of the wearable device 10 into a preferable state. It should be noted that, when the operation of the PPG sensor section 122 is stopped, it is preferable to present it to a user. In addition, the present embodiment is not limited to stopping the operation of the PPG sensor section 122, but other operations such as communication between the wearable device 10 and the server 30 may be stopped.

In addition, in this method, the reliability degree $r_i$ may be fed back to the processing of the detection section 332, correction section 336 and HRV index calculation section 342 of the server 30. Specifically, in a case where the period in which the reliability degree $r_i$ is lower than a predetermined value continues for a predetermined time (e.g., several seconds) or longer, it is determined to be difficult to appropriately detect an abnormal value, appropriately correct an abnormal value, and appropriately calculate an HRV index. Therefore, in this method, the detection of an abnormal value by the detection section 332, the correction of an abnormal value by the correction section 336, and the calculation of an HRV index by the HRV index calculation section 342 are temporarily stopped in such a case. As a result, stopping the operations of the detection section 332, the correction section 336, and the HRV index calculation section 342 makes it possible to suppress an increase in the processing resources (such as the amount of processing, the amount of hold memories, and the amount of retained data) of the server 30. In other words, according to this method, feeding back the reliability degree $r_i$ to the server 30 makes it possible to bring the processing operation of the server 30 into a preferable state.

In addition, in this method, the reliability degree $r_i$ may be fed back to the HRV index calculation section 342 of the server 30 to control the calculation processing of the HRV index. Specifically, in this method, the time series data of PPIs acquired in the period in which the reliability degree $r_i$ is lower than a predetermined value is excluded from the data used to calculate the HRV index. By doing so, it is possible to acquire an HRV index having higher reliability. For example, it is sometimes desirable to use the average value of the HRV indices calculated for the last month for a certain user to manage the physical condition of the user. In such a case, excluding the time series data of PPIs in a period in which the reliability degree $r_i$ is low and calculating the average value of HRV indices make it possible to acquire the average value of HRV indices in which the state of the user is more precisely reflected, and effectively use it to manage the physical condition of the user.

In addition, in this method, in a case where a predetermined index is calculated by integrating HRV indices in a plurality of periods, the integrated value described above may be calculated after weighting processing is performed on each HRV index on the basis of the reliability degree $r_i$ in each period. More specifically, the degree of stress of a user for a day is sometimes defined as a weighted average of a plurality of SDNNs (a type of HRV indies) calculated during the day. In this method, weighting processing is performed to provide a large weight to the value of an SDNN in a section in which the high reliability degree $r_i$ is high, and provide a small weight to an SDNN in a section in which the low reliability degree $r_i$ is low in such a case. Such weighting makes it possible to suppress the influence of the SDNN in the section in which it is not possible to appropriately measure pulse wave signals and the reliability degree $r_i$ is low, on the degree of stress described above, and acquire the degree of stress with high reliability. In other words, according to this method, feeding back the reliability degree $r_i$ to the calculation processing of the server 30 makes it possible to further increase the accuracy of an HRV index, the degree of stress, and the like calculated by the server 30.

5. CONCLUSION

As described above, according to the present embodiment, calculating the reliability degree of the measurement of pulse wave signals and presenting the reliability degree described above to a user together with an HRV index and the like make it possible to guide the state of the user to a state ideal for the measurement. Further, feeding back the calculated reliability degree to the control of the wearable device 10 or the server 30 makes it possible to preferably control the wearable device 10 or the server 30 such as accurately calculating an HRV index and suppressing the amount of battery consumption. In other words, according to the present embodiment, it is possible in the measurement of pulse wave signals for a user freely moving around to bring the measurement into a preferable state.

Further, according to the present embodiment, accurately detecting an abnormal value from time series data of PPIs and correcting the time series data of PPIs on the basis of the detected abnormal value make it possible to prevent an HRV index or the like to be calculated from deviating from a correct normal HRV index or the like that should be calculated. In other words, according to the present embodiment, it is possible to increase the accuracy of an HRV index or the like calculated on the basis of time series data of PPIs.

6. REGARDING HARDWARE CONFIGURATION

FIG. 26 is an explanatory diagram describing an example of a hardware configuration of an information processing apparatus 900 according to the present embodiment. In FIG. 26, the information processing apparatus 900 exemplifies the hardware configuration of the server 30.

The information processing apparatus 900 includes, for example, a CPU 950, a ROM 952, a RAM 954, a recording medium 956, an input/output interface 958, and an operation input device 960. Further, the information processing apparatus 900 includes a display device 962, a communication interface 968, and a sensor 980. In addition, the information processing apparatus 900 uses, for example, a bus 970 as a transmission path of data to couple the respective components with each other.

(CPU 950)

The CPU 950 includes, for example, one or two or more processors each including an arithmetic circuit such as a CPU, various processing circuits, and the like, and functions as a control unit (e.g., control unit 130 described above) that controls the entire information processing apparatus 900. Specifically, the CPU 950 attains the functions of, for example, the detection section 332, the detection correction control section 334, the correction section 336, the reliability degree calculation section 338, the HRV index calculation section 342, and the like described above in the information processing apparatus 900.

(ROM 952 and RAM 954)

The ROM 952 stores data or the like for control such as programs and operation parameters used by the CPU 950. The RAM 954 temporarily stores, for example, a program or the like executed by the CPU 950.

(Recording Medium 956)

The recording medium 956 functions as the storage unit 350 described above, and stores, for example, data for the information processing method according to the present embodiment and various kinds of data such as various applications. Here, examples of the recording medium 956 include a magnetic recording medium such as a hard disk, and a nonvolatile memory such as a flash memory. The recording medium 956 may be detachably attached to the information processing apparatus 900.

(Input/Output Interface 958, Operation Input Device 960, and Display Device 962)

The input/output interface 958 couples, for example, the operation input device 960, the display device 962, and the like to each other. Examples of the input/output interface 958 include a USB (Universal Serial Bus) terminal, a DVI (Digital Visual Interface) terminal, an HDMI (High-Definition Multimedia Interface) (registered trademark) terminal, various processing circuits, and the like.

The operation input device 960 functions, for example, as the input unit 300 described above, and the operation input device 960 is coupled to the input/output interface 958 inside the information processing apparatus 900.

The display device 962 functions, for example, as the output unit 310 described above, and the display device 962 is provided on the information processing apparatus 900, and is coupled to the input/output interface 958 inside the information processing apparatus 900. Examples of the display device 962 include a liquid crystal display, an organic electro-luminescence display, and the like It should be noted that it is also possible to couple the input/output interface 958 to an external device such as an external operation input device (e.g., keyboard, mouse, or the like) of the information processing apparatus 900, and an external display device. In addition, the input/output interface 958 may be coupled to a drive (not illustrated). The drive is a reader/writer for a removable recording medium such as a magnetic disk, an optical disc, or a semiconductor memory, and built in or externally attached to the information processing apparatus 900. The drive reads out information recorded on the mounted removable recording medium, and outputs the information to the RAM 954. In addition, the drive is also able to write the record into the mounted removable recording medium.

(Communication Interface 968)

The communication interface 968 functions as the communication unit 340 for performing wireless or wired communication with an external device such as the server 30, for example, via the network 70 described above (or directly). Here, examples of the communication interface 968 include a communication antenna and an RF (Radio frequency) circuit (wireless communication), an IEEE 802.15.1 port and a transmission/reception circuit (wireless communication), an IEEE 802.11 port and a transmission/reception circuit (wireless communication), a LAN (Local Area Network) terminal and a transmission/reception circuit (wired communication), or the like.

(Sensor 980)

The sensor 980 functions as the sensor unit 120 of the wearable device 10. Further, the sensor 980 may include various sensors such as a pressure sensor.

The example of the hardware configuration of the information processing apparatus 900 has been demonstrated above. It should be noted that the hardware configuration of the information processing apparatus 900 is not limited to the configuration illustrated in FIG. 26. Specifically, each of the components described above may be configured using a general-purpose member, or may be configured by using hardware dedicated to the function of each component. The configuration may be changed as appropriate in accordance with the technical level at the time of carrying out the present disclosure.

For example, the information processing apparatus 900 does not have to include the communication interface 968 in a case where the information processing apparatus 900 communicates with an external device or the like via a coupled external communication device, or in a case where the information processing apparatus 900 is configured to perform processing in a stand-alone manner. In addition, the communication interface 968 may have a component that is communicable with one or two or more external devices in a plurality of communication schemes. In addition, it is also possible to configure the information processing apparatus 900 without providing the recording medium 956, the operation input device 960, the display device 962, or the like.

In addition, the information processing apparatus 900 according to the present embodiment may be applied to a system including a plurality of apparatuses that is supposed to be coupled to a network (or communicate with each other) like, for example, cloud computing. In other words, it is also possible to achieve the information processing apparatus 900 according to the present embodiment described above, for example, as an information processing system that performs processing according to the information processing method according to the present embodiment by using a plurality of apparatuses.

7. SUPPLEMENT

It should be noted that the embodiment of the present disclosure described above may include, for example, a program for causing a computer to function as an information processing apparatus according to the present embodiment, and a non-transitory tangible medium having the program recorded thereon. In addition, the program may be distributed via a communication line (including wireless communication) such as the Internet.

In addition, the steps of the processing according to each of each embodiment described above do not necessarily have to be executed in the described order. For example, the order in which the respective steps are executed may be changed as appropriate. In addition, the respective steps may be partially executed in parallel or individually instead of being executed in chronological order. Furthermore, the processing method of each step does not necessarily have to be processed in accordance with the described method, but may be processed in another method by another functional unit, for example.

A preferred embodiment(s) of the present disclosure has/have been described above in detail with reference to the accompanying drawings, but the technical scope of the present disclosure is not limited to such an embodiment(s). It is apparent that a person having ordinary skill in the art of the present disclosure may arrive at various alterations and modifications within the scope of the technical idea described in the appended claims, and it is understood that such alterations and modifications naturally fall within the technical scope of the present disclosure.

In addition, the effects described herein are merely illustrative and exemplary, and not limitative. In other words, the technique according to the present disclosure may attain other effects that are apparent to those skilled in the art from the description herein, in addition to the effects described above or in place of the effects described above.

It should be noted that the following configurations are also fall within the technical scope of the present disclosure.

(1)
An information processing apparatus including:
a reliability degree calculation section that calculates a reliability degree of pulsation variability data or a body index, the pulsation variability data being acquired from sensing data acquired by a pulse wave sensor worn by a user, the body index being calculated from the pulsation variability data and indicating a physical state of the user; and
a control unit that controls various kinds of processing on the basis of the calculated reliability degree.

(2)
The information processing apparatus according to (1), in which the reliability degree is calculated on the basis of at least one of a state of the user, a wearing state of the pulse wave sensor, or the acquired pulsation variability data.

(3)
The information processing apparatus according to (2), in which the reliability degree is calculated on the basis of the state of the user, the state being acquired by a motion sensor worn by the user.

(4)
The information processing apparatus according to (2), in which the reliability degree is calculated on the basis of the wearing state of the pulse wave sensor, the wearing state being acquired by a sensor worn by the user together with the pulse wave sensor.

(5)
The information processing apparatus according to (1), further including a detection section that detects an abnormal value from the pulsation variability data.

(6)
The information processing apparatus according to (5), in which the reliability degree is calculated on the basis of the detected abnormal value.

(7)
The information processing apparatus according to (5) or (6), in which the control unit controls the detection section on the basis of the calculated reliability degree.

(8)
The information processing apparatus according to any one of (5) to (7), in which the detection section detects the abnormal value by extracting the pulsation variability data in a section of a predetermined length from the pulsation variability data, and comparing the extracted pulsation variability data in the section of the predetermined length with a predetermined pattern.

(9)
The information processing apparatus according to any one of (5) to (8), in which the detection section changes a parameter, the parameter being used to detect the abnormal value in accordance with a physical characteristic of the user.

(10)
The information processing apparatus according to (5), further including a correction section that corrects the pulsation variability data on the basis of the detected abnormal value.

(11)
The information processing apparatus according to (10), in which the control unit controls the correction section on the basis of the calculated reliability degree.

(12)
The information processing apparatus according to (10) or (11), in which the correction section changes correction processing in accordance with a type of the body index to be calculated.

(13)
The information processing apparatus according to (10) or (11), in which the correction section extracts the pulsation variability data in a section of a predetermined length from the pulsation variability data, recognizes a pattern of the extracted pulsation variability data in the section of the predetermined length, and changes correction processing in accordance with a type of the recognized pattern.

(14)

The information processing apparatus according to (10), further including an index calculation section that calculates the body index on the basis of the corrected pulsation variability data.

(15)

The information processing apparatus according to (14), in which the control unit controls the index calculation section on the basis of the calculated reliability degree.

(16)

The information processing apparatus according to (14), in which the index calculation section weights the pulsation variability data or the body index in each section on the basis of the reliability degree.

(17)

The information processing apparatus according to (1), in which the control unit controls the pulse wave sensor on the basis of the calculated reliability degree.

(18)

The information processing apparatus according to (1), in which the control unit controls at least one of detection processing of detecting an abnormal value from the pulsation variability data, correction processing of correcting the pulsation variability data, or calculation processing of calculating the body index from the pulsation variability data, the detection processing, the correction processing, and the calculation processing being performed in the information processing apparatus.

(19)

An information processing method including:

calculating a reliability degree of pulsation variability data or a body index, the pulsation variability data being acquired from sensing data acquired by a pulse wave sensor worn by a user, the body index being calculated from the pulsation variability data and indicating a physical state of the user; and controlling various kinds of processing on the basis of the calculated reliability degree.

(20)

A program for causing a computer to implement:

a function of calculating a reliability degree of pulsation variability data or a body index, the pulsation variability data being acquired from sensing data acquired by a pulse wave sensor worn by a user, the body index being calculated from the pulsation variability data and indicating a physical state of the user; and a function of controlling various kinds of processing on the basis of the calculated reliability degree.

REFERENCE SIGNS LIST

1: Information processing system
10, 10a: Wearable device
12: Band portion
14: Pressure sensor section
30: Server
50: User terminal
70: Network
100, 300: Input unit
110, 310: Output unit
120: Sensor unit
122: PPG sensor section
124: Motion sensor section
130, 330: Control unit
140, 340: Communication unit
150, 350: Storage unit
200: Measurement site
202: Blood vessel
332: Detection section
334: Detection correction control section
336: Correction section
338: Reliability degree calculation section
342: HRV index calculation section
350: Storage unit
352: DB
500: Gray-out display
900: Information processing apparatus
950: CPU
952: ROM
954: RAM
956: Recording medium
958: Input/output interface
960: Operation input device
962: Display device
968: Communication interface
970: Bus
980: Sensor

The invention claimed is:

1. An information processing apparatus, comprising:
a processor configured to:
acquire time series data of pulse rate intervals from pulse wave signals outputted from a pulse wave sensor worn by a user;
calculate a reliability degree of one of the time series data of the pulse rate intervals or a heart rate variability (HRV) index, wherein
the HRV index is calculated from the time series data of the pulse rate intervals, and
the reliability degree changes based on a deviation of a physical state of the user at a time of measurement of the pulse wave signals from a resting state; and
control a plurality of processing operations based on the calculated reliability degree.

2. The information processing apparatus according to claim 1, wherein the reliability degree is calculated based on at least one of the physical state of the user, a wearing state of the pulse wave sensor, or the acquired time series data of the pulse rate intervals.

3. The information processing apparatus according to claim 2, wherein
the reliability degree is calculated further based on the physical state of the user, and
the physical state is acquired by a motion sensor worn by the user.

4. The information processing apparatus according to claim 2, wherein
the reliability degree is calculated further based on the wearing state of the pulse wave sensor, and
the wearing state is acquired by a sensor worn by the user together with the pulse wave sensor.

5. The information processing apparatus according to claim 1, wherein the processor is further configured to detect an abnormal value from the time series data of the pulse rate intervals.

6. The information processing apparatus according to claim 5, wherein the reliability degree is calculated based on the detected abnormal value.

7. The information processing apparatus according to claim 5, wherein the processor is further configured to control detection of the abnormal value based on the calculated reliability degree.

8. The information processing apparatus according to claim 5, wherein the processor is further configured to:

detect the abnormal value based on extraction of the time series data of the pulse rate intervals in a section of a specific time period from the time series data of the pulse rate intervals; and compare the extracted time series data of the pulse rate intervals in the section of the specific time period with a specific pattern.

9. The information processing apparatus according to claim 5, wherein the processor is further configured to change a parameter, and the parameter is used to detect the abnormal value in accordance with a physical characteristic of the user.

10. The information processing apparatus according to claim 5, wherein the processor is further configured to correct the time series data of the pulse rate intervals based on the detected abnormal value.

11. The information processing apparatus according to claim 10, wherein the processor is further configured to correct the time series data of the pulse rate intervals based on the calculated reliability degree.

12. The information processing apparatus according to claim 10, wherein the processor is further configured to:

calculate a plurality of HRV indices based on the corrected time series data of the pulse rate intervals; and change correction processing operation based on a type of the HRV index to be calculated, wherein the plurality of HRV indices includes the HRV index.

13. The information processing apparatus according to claim 10, wherein the processor is further configured to:

extract the time series data of the pulse rate intervals in a section of a specific time period from the time series data of the pulse rate intervals;

recognize a pattern of the extracted time series data of the pulse rate intervals in the section of the specific time period; and change correction processing based on a type of the recognized pattern.

14. The information processing apparatus according to claim 10, wherein the processor is further configured to calculate the HRV index based on the time series data of the pulse rate intervals.

15. The information processing apparatus according to claim 14, wherein the processor is further configured to calculate the HRV index based on the calculated reliability degree.

16. The information processing apparatus according to claim 14, wherein the processor is further configured to weigh one of the time series data of the pulse rate intervals or the HRV index based on the reliability degree.

17. The information processing apparatus according to claim 1, wherein the processor is further configured to control the pulse wave sensor based on the calculated reliability degree.

18. The information processing apparatus according to claim 1, wherein the plurality of processing operations includes at least one of a detection processing operation of detecting an abnormal value from pulsation variability data, a correction processing operation of correcting the pulsation variability data, or a calculation processing operation of calculating the HRV index from the pulsation variability data, and the detection processing operation, the correction processing operation, and the calculation processing operation are performed in the information processing apparatus.

19. An information processing method, comprising:

acquiring time series data of pulse rate intervals from pulse wave signals outputted from a pulse wave sensor worn by a user;

calculating a reliability degree of one of the time series data of the pulse rate intervals or a heart rate variability (HRV) index, wherein the HRV index is calculated from the time series data of the pulse rate intervals, and the reliability degree changes based on a deviation of a physical state of the user at a time of measurement of the pulse wave signals from a resting state; and controlling a plurality of processing operations based on the calculated reliability degree.

20. A non-transitory computer-readable medium having stored thereon, computer-executable instructions which, when executed by a computer, cause the computer to execute operations, the operations comprising:

acquiring time series data of pulse rate intervals from pulse wave signals outputted from a pulse wave sensor worn by a user;

calculating a reliability degree of one of the time series data of the pulse rate intervals or a heart rate variability (HRV) index, wherein the HRV index is calculated from the time series data of the pulse rate intervals, and the reliability degree changes based on a deviation of a physical state of the user at a time of measurement of the pulse wave signals from a resting state; and controlling a plurality of processing operations based on the calculated reliability degree.

\* \* \* \* \*